(12) United States Patent
Ducarouge et al.

(10) Patent No.: US 12,162,932 B2
(45) Date of Patent: Dec. 10, 2024

(54) COMBINED TREATMENT WITH NETRIN-1 INTERFERING DRUG AND IMMUNE CHECKPOINT INHIBITORS DRUGS

(71) Applicants: NETRIS PHARMA, Lyons (FR); Universite Claude Bernard Lyon 1, Villeurbanne (FR); Centre national de la recherche scientifique, Paris (FR); Centre Léon-Bérard, Lyons (FR); INSTITUT NATIONAL DE LA SANTE ET DE LA RECHERCHE MEDICALE (INSERM), Paris (FR)

(72) Inventors: Benjamin Ducarouge, La Tour du Pin (FR); David Goldschneider, Villeurbanne (FR); Anna Maria Rita Redavid, Rutigliano (IT); Benjamin Gibert, Villeurbanne (FR); Patrick Mehlen, Serezin-de-la-Tour (FR)

(73) Assignees: Netris Pharma, Lyons (FR); Université Claude Bernard Lyon 1, Villeurbanne (FR); Centre national de la Recherche Scientifique, Paris (FR); Centre Léon-Bérard, Lyons (FR); Institut National de la Sante et de la Recherche Medicale, Paris (FR)

(*) Notice: Subject to any disclaimer, the term of this patent is extended or adjusted under 35 U.S.C. 154(b) by 452 days.

(21) Appl. No.: 16/476,239

(22) PCT Filed: Jan. 5, 2018

(86) PCT No.: PCT/EP2018/050289
§ 371 (c)(1),
(2) Date: Jul. 5, 2019

(87) PCT Pub. No.: WO2018/127570
PCT Pub. Date: Jul. 12, 2018

(65) Prior Publication Data
US 2019/0315852 A1    Oct. 17, 2019

(30) Foreign Application Priority Data
Jan. 5, 2017    (EP) .................................... 17305014

(51) Int. Cl.
| | | |
|---|---|---|
| *C07K 16/22* | (2006.01) | |
| *A61K 39/395* | (2006.01) | |
| *A61P 35/00* | (2006.01) | |
| *C07K 16/28* | (2006.01) | |
| *C07K 16/30* | (2006.01) | |
| *A61K 39/00* | (2006.01) | |

(52) U.S. Cl.
CPC .............. *C07K 16/22* (2013.01); *A61P 35/00* (2018.01); *C07K 16/2818* (2013.01); *C07K 16/30* (2013.01); *A61K 39/395* (2013.01); *A61K 2039/507* (2013.01); *C07K 2317/565* (2013.01); *C07K 2317/76* (2013.01)

(58) Field of Classification Search
CPC .... C07K 16/22; C07K 16/2818; C07K 16/30; C07K 2317/565; C07K 2317/76; A61P 35/00; A61K 2039/507; A61K 2300/00; A61K 2039/505; A61K 39/395
See application file for complete search history.

(56) References Cited

U.S. PATENT DOCUMENTS

| | | | |
|---|---|---|---|
| 9,683,048 B2 * | 6/2017 | Freeman | A61P 31/00 |
| 10,494,427 B2 * | 12/2019 | Delcros | C07K 16/22 |
| 2018/0072800 A1 | 3/2018 | Delcros et al. | |
| 2018/0161302 A1 | 6/2018 | Kremmidiotis et al. | |
| 2019/0315852 A1 | 10/2019 | Ducarouge et al. | |
| 2020/0079842 A1 | 3/2020 | Delcros et al. | |
| 2021/0069147 A1 | 3/2021 | Kremmidiotis et al. | |

FOREIGN PATENT DOCUMENTS

| | | | | |
|---|---|---|---|---|
| CN | 104083762 | | 10/2014 | |
| WO | WO-2015104360 A1 * | | 7/2015 | A61K 39/395 |

OTHER PUBLICATIONS

Black M, Barsoum IB, Truesdell P, et al. Activation of the PD-1/PD-L1 immune checkpoint confers tumor cell chemoresistance associated with increased metastasis. Oncotarget. 2016;7(9): 10557-10567. doi:10.18632/oncotarget.7235 (Year: 2016).*

Black M, Barsoum IB, Truesdell P, Cotechini T, Macdonald-Goodfellow SK, Petroff M, Siemens DR, Koti M, Craig AW, Graham CH. Activation of the PD-1/PD-L1 immune checkpoint confers tumor cell chemoresistance associated with increased metastasis. Oncotarget. Mar. 1, 2016;7(9):10557-67. (Year: 2016).*

Murphy et al. (Journal of Immunological Methods, vol. 463, p. 127-133, 2018) (Year: 2018).*

Chen (Sci Adv. Apr. 1, 2020;6(14):eaaz7825) (Year: 2020).*

Edwards et al. 2003. The remarkable flexibility of the human antibody repertoire; isolation of over one thousand different antibodies to a single protein, BlyS. Journal of Molecular Biology 334:103-118 (Year: 2003).*

Hamanishi, J., Mandai, M., Matsumura, N et al. PD-1/PD-L1 blockade in cancer treatment: perspectives and issues. Int J Clin Oncol 21, 462-473 (2016). (Year: 2016).*

(Continued)

*Primary Examiner* — Hong Sang
(74) *Attorney, Agent, or Firm* — B. Aaron Schulman, Esq.; Stites & Harbison, PLLC

(57) ABSTRACT

The invention is the combination or combined use of (i) a compound able to disrupt or impede netrin-1/netrin-1 receptors interaction or netrin-1-mediated receptor dimerization, also called herein a NTN1 neutralizing agent, which compound may be an antibody binding to netrin-1 or anti-netrin-1 antibody, and (ii) an immune checkpoint inhibitor, in the treatment of cancer. The composition may comprise an anti-netrin-1 antibody and an immune checkpoint inhibitor, for use as an anticancerous drug with a simultaneous, separate or sequential administration of the anti-netrin-1 antibody and the immune checkpoint inhibitor to a patient.

10 Claims, 3 Drawing Sheets

Figures 1, 2, 4:
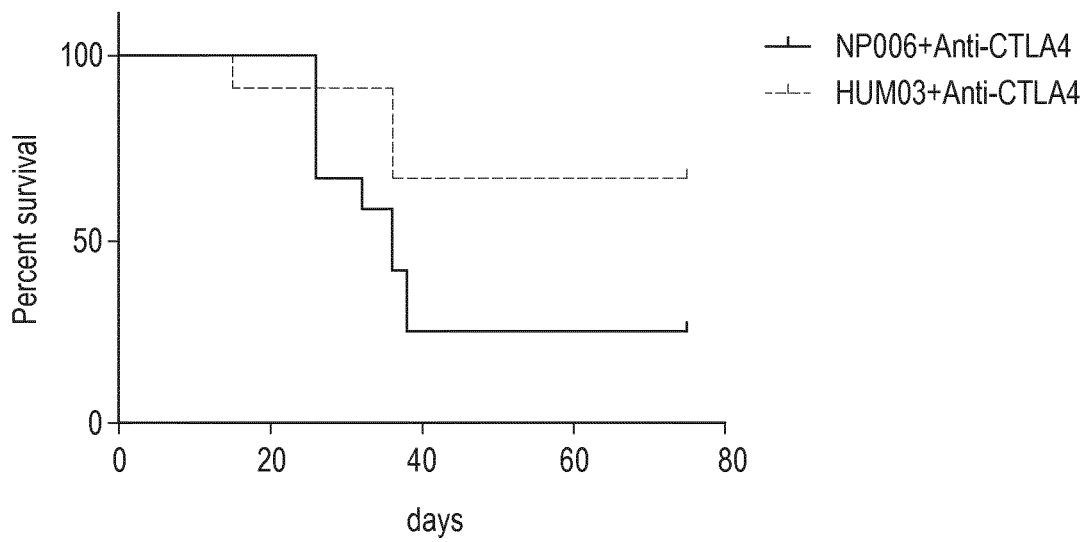

Specification includes a Sequence Listing.

(56) References Cited

OTHER PUBLICATIONS

Ramkhelawon et al.; Netrin-1 promotes adipose tissue macrophage retention and insulin resistance in obesity/Nat Med. Apr. 2014;20 (4):377-84. Epub Mar. 2, 2014.
Grandin et al.; Structural Decoding of the Netrin-1/UNC5 Interaction and its Therapeutical Implications in Cancers/Cancer Cell. Feb. 8, 2016;29(2):173-85.
Boneschansker et al.; Netrin-1 Augments Chemokinesis in CD4+T Cells In Vitro and Elicits a Proinflammatory Response in Vivo/ J. Immunol, Aug. 15, 2016, 197 (4) 1389-1398pp.
European Search Report for EP 17 30 5014, dated Jun. 8, 2017.
International Search Report for PCT/EP2018/050289, dated Mar. 23, 2018.
Written Opinion of the International Searching Authority for PCT/EP2018/050289, dated Mar. 23, 2018.

* cited by examiner

| NP006 | HUM03 | Anti-CTLA4+ NP006 | Anti-CTLA4+ HUM03 |
|---|---|---|---|
| 0/12 | 0/12 | 2/12 | 8/12 p=0.0394 (Mantel Cox) |

| PBS | Anti-PD1+NP006 | Anti-PD1+HUM03 |
|---|---|---|
| 4/7 | 4/7 | 7/7 p=0.0411 (Mantel Cox) |

```
                     SEQUENCE LISTING

<160> NUMBER OF SEQ ID NOS: 36

<210> SEQ ID NO 1
<211> LENGTH: 604
<212> TYPE: PRT
<213> ORGANISM: Homo sapiens
<220> FEATURE:
<221> NAME/KEY: SIGNAL
<222> LOCATION: (1)..(24)
<220> FEATURE:
<221> NAME/KEY: MISC_FEATURE
<222> LOCATION: (339)..(381)
<223> OTHER INFORMATION: linear epitope

<400> SEQUENCE: 1

Met Met Arg Ala Val Trp Glu Ala Leu Ala Leu Ala Ala Val Ala
1               5                   10                  15

Cys Leu Val Gly Ala Val Arg Gly Gly Pro Gly Leu Ser Met Phe Ala
                20                  25                  30

Gly Gln Ala Ala Gln Pro Asp Pro Cys Ser Asp Glu Asn Gly His Pro
            35                  40                  45

Arg Arg Cys Ile Pro Asp Phe Val Asn Ala Ala Phe Gly Lys Asp Val
        50                  55                  60
```

-continued

```
Arg Val Ser Ser Thr Cys Gly Arg Pro Pro Ala Arg Tyr Cys Val Val
 65                  70                  75                  80

Ser Glu Arg Gly Glu Arg Leu Arg Ser Cys His Leu Cys Asn Ala
                 85                  90                  95

Ser Asp Pro Lys Lys Ala His Pro Pro Ala Phe Leu Thr Asp Leu Asn
                100                 105                 110

Asn Pro His Asn Leu Thr Cys Trp Gln Ser Glu Asn Tyr Leu Gln Phe
            115                 120                 125

Pro His Asn Val Thr Leu Thr Leu Ser Leu Gly Lys Lys Phe Glu Val
        130                 135                 140

Thr Tyr Val Ser Leu Gln Phe Cys Ser Pro Arg Pro Glu Ser Met Ala
145                 150                 155                 160

Ile Tyr Lys Ser Met Asp Tyr Gly Arg Thr Trp Val Pro Phe Gln Phe
                165                 170                 175

Tyr Ser Thr Gln Cys Arg Lys Met Tyr Asn Arg Pro His Arg Ala Pro
                180                 185                 190

Ile Thr Lys Gln Asn Glu Gln Glu Ala Val Cys Thr Asp Ser His Thr
            195                 200                 205

Asp Met Arg Pro Leu Ser Gly Gly Leu Ile Ala Phe Ser Thr Leu Asp
210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
                245                 250                 255

Phe Gly Asp Glu Asn Glu Asp Ser Glu Leu Ala Arg Asp Ser Tyr
                260                 265                 270

Phe Tyr Ala Val Ser Asp Leu Gln Val Gly Gly Arg Cys Lys Cys Asn
            275                 280                 285

Gly His Ala Ala Arg Cys Val Arg Asp Arg Asp Asp Ser Leu Val Cys
        290                 295                 300

Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
                325                 330                 335

Glu Cys Val Ala Cys Asn Cys Asn Leu His Ala Arg Arg Cys Arg Phe
                340                 345                 350

Asn Met Glu Leu Tyr Lys Leu Ser Gly Arg Lys Ser Gly Gly Val Cys
            355                 360                 365

Leu Asn Cys Arg His Asn Thr Ala Gly Arg His Cys His Tyr Cys Lys
        370                 375                 380

Glu Gly Tyr Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
                405                 410                 415

Asn Gln Thr Thr Gly Gln Cys Pro Cys Lys Asp Gly Val Thr Gly Ile
                420                 425                 430

Thr Cys Asn Arg Cys Ala Lys Gly Tyr Gln Gln Ser Arg Ser Pro Ile
        435                 440                 445

Ala Pro Cys Ile Lys Ile Pro Val Ala Pro Pro Thr Thr Ala Ala Ser
            450                 455                 460

Ser Val Glu Glu Pro Glu Asp Cys Asp Ser Tyr Cys Lys Ala Ser Lys
465                 470                 475                 480

Gly Lys Leu Lys Ile Asn Met Lys Lys Tyr Cys Lys Lys Asp Tyr Ala
```

|  | 485 |  |  | 490 |  |  | 495 |  |
|---|---|---|---|---|---|---|---|---|

Val Gln Ile His Ile Leu Lys Ala Asp Lys Ala Gly Asp Trp Trp Lys
             500               505                510

Phe Thr Val Asn Ile Ile Ser Val Tyr Lys Gln Gly Thr Ser Arg Ile
     515                   520                525

Arg Arg Gly Asp Gln Ser Leu Trp Ile Arg Ser Arg Asp Ile Ala Cys
         530                 535              540

Lys Cys Pro Lys Ile Lys Pro Leu Lys Lys Tyr Leu Leu Leu Gly Asn
545                550               555              560

Ala Glu Asp Ser Pro Asp Gln Ser Gly Ile Val Ala Asp Lys Ser Ser
             565               570              575

Leu Val Ile Gln Trp Arg Asp Thr Trp Ala Arg Arg Leu Arg Lys Phe
         580                 585              590

Gln Gln Arg Glu Lys Lys Gly Lys Cys Lys Lys Ala
     595                 600

<210> SEQ ID NO 2
<211> LENGTH: 1817
<212> TYPE: DNA
<213> ORGANISM: Homo sapiens

<400> SEQUENCE: 2

```
atgatgcgcg cagtgtggga ggcgctggcg gcgctggcgg cggtggcgtg cctggtgggc      60
gcggtgcgcg gcgggcccgg gctcagcatg ttcgcgggcc aggcggcgca gcccgatccc     120
tgctcggacg agaacggcca cccgcgccgc tgcatcccgg actttgtcaa tgcggccttc     180
ggcaaggacg tgcgcgtgtc cagcacctgc ggccggcccc ggcgcgcta ctgcgtggtg      240 agcgagcgcg cgaggagcg gctgcgctcg tgccacctct gcaacgcgtc cgaccccaag      300
aaggcgcacc cgcccgcctt cctcaccgac ctcaacaacc gcacaacct gacgtgctgg      360 cagtccgaga actacctgca gttcccgcac aacgtcacgc tcacactgtc cctcggcaag      420
aagttcgaag tgacctacgt gagcctgcag ttctgctcgc cgcggcccga gtccatggcc      480
atctacaagt ccatggacta cggggcgcacg tgggtgccct ccagttcta ctccacgcag      540 tgccgcaaga tgtacaaccg gccgcaccgc gcgcccatca ccaagcagaa cgagcaggag      600
gccgtgtgca ccgactcgca caccgacatg cgcccgctct cgggcggcct catcgccttc      660
agcacgctgg acgggcggcc ctcggcgcac gacttcgaca actcgcccgt gctgcaggac      720
tgggtcacgg ccacagacat ccgcgtggcc ttcagccgcc tgcacacgtt cggcgacgag      780
aacgaggacg actcggagct ggcgcgcgac tcgtacttct acgcggtgtc cgacctgcag      840
gtgggcggcc ggtgcaagtg caacggccac gcggcccgct gcgtgcgcga ccgcgacgac      900
agcctggtgt gcgactgcag gcacaacacg ccggcccgg agtgcgaccg ctgcaagccc      960
ttccactacg accggccctg gcagcgcgcc acagcccgcg aagccaacga gtgcgtggcc     1020
tgtaactgca acctgcatgc ccggcgctgc cgcttcaaca tggagctcta caagctttcg     1080
gggcgcaaga gcggaggtgt ctgcctcaac tgtcgccaca caccgccgg ccgccactgc     1140 cattactgca aggaggggcta ctaccgcgac atgggcaagc ccatcaccca ccggaaggcc     1200
tgcaaagcct gtgattgcca ccctgtgggt gctgctggca aaacctgcaa ccaaaccacc     1260
ggccagtgtc cctgcaagga cggcgtgacg gtatcacct gcaaccgctg cgccaaaggc     1320
taccagcaga gccgctctcc catcgccccc tgcataaaga tccctgtagc gccgccgacg     1380
actgcagcca gcagcgtgga ggagcctgaa gactgcgatt cctactgcaa ggcctccaag     1440
```

```
gggaagctga agattaacat gaaaaagtac tgcaagaagg actatgccgt ccagatccac    1500
atcctgaagg cggacaaggc gggggactgg tggaagttca cggtgaacat catctccgtg    1560
tataagcagg gcacgagccg catccgccgc ggtgaccaga gcctgtggat ccgctcgcgg    1620
gacatcgcct gcaagtgtcc caaaatcaag cccctcaaga agtacctgct gctgggcaac    1680
gcggaggact ctccggacca gagcggcatc gtggccgata aaagcagcct ggtgatccag    1740
tggcgggaca cgtgggcgcg gcggctgcgc aagttccagc agcgtgagaa gaagggcaag    1800
tgcaagaagg cctagcg                                                   1817

<210> SEQ ID NO 3
<211> LENGTH: 43
<212> TYPE: PRT
<213> ORGANISM: Homo sapiens

<400> SEQUENCE: 3

Val Ala Cys Asn Cys Asn Leu His Ala Arg Arg Cys Arg Phe Asn Met
1               5                   10                  15

Glu Leu Tyr Lys Leu Ser Gly Arg Lys Ser Gly Val Cys Leu Asn
            20                  25                  30

Cys Arg His Asn Thr Ala Gly Arg His Cys His
        35                  40

<210> SEQ ID NO 4
<211> LENGTH: 129
<212> TYPE: DNA
<213> ORGANISM: Homo sapiens

<400> SEQUENCE: 4
gtggcctgta actgcaacct gcatgcccgg cgctgccgct tcaacatgga gctctacaag    60
cttttcgggc gcaagagcgg aggtgtctgc ctcaactgtc gccacaacac cgccggccgc   120
cactgccat                                                            129

<210> SEQ ID NO 5
<211> LENGTH: 8
<212> TYPE: PRT
<213> ORGANISM: Mus musculus

<400> SEQUENCE: 5

Gly Tyr Thr Phe Thr Ser Tyr Asn
1               5

<210> SEQ ID NO 6
<211> LENGTH: 8
<212> TYPE: PRT
<213> ORGANISM: Mus musculus

<400> SEQUENCE: 6

Ile Tyr Pro Gly Asn Gly Asp Thr
1               5

<210> SEQ ID NO 7
<211> LENGTH: 9
<212> TYPE: PRT
<213> ORGANISM: Mus musculus

<400> SEQUENCE: 7

Ala Arg Gly Gly Thr Gly Phe Ala Tyr
1               5
```

```
<210> SEQ ID NO 8
<211> LENGTH: 6
<212> TYPE: PRT
<213> ORGANISM: Mus musculus

<400> SEQUENCE: 8

Gln Ser Val Ser Asn Asp
1               5

<210> SEQ ID NO 9
<211> LENGTH: 9
<212> TYPE: PRT
<213> ORGANISM: Mus musculus

<400> SEQUENCE: 9

Gln Gln Asp Tyr Ser Ser Pro Trp Thr
1               5

<210> SEQ ID NO 10
<211> LENGTH: 116
<212> TYPE: PRT
<213> ORGANISM: Mus musculus
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 10

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Thr Gly Phe Ala Tyr Trp Gly Gln Gly Thr Leu Val
            100                 105                 110

Thr Val Ser Ala
        115

<210> SEQ ID NO 11
<211> LENGTH: 107
<212> TYPE: PRT
<213> ORGANISM: Mus musculus
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
```

```
<221> NAME/KEY: MISC_FEATURE
<222> LOCATION: (89)..(97)
<223> OTHER INFORMATION: CDR according to IGMT

<400> SEQUENCE: 11

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 12
<211> LENGTH: 440
<212> TYPE: PRT
<213> ORGANISM: Mus musculus
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 12

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Thr Gly Phe Ala Tyr Trp Gly Gln Gly Thr Leu Val
            100                 105                 110

Thr Val Ser Ala Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Glu Ser Asp
                165                 170                 175
```

```
Leu Tyr Thr Leu Ser Ser Val Thr Val Pro Ser Ser Pro Arg Pro
                180                 185                 190

Ser Glu Thr Val Thr Cys Asn Val Ala His Pro Ala Ser Ser Thr Lys
            195                 200                 205

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
    370                 375                 380

Lys Asn Thr Gln Pro Ile Met Asn Thr Asn Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
        435                 440

<210> SEQ ID NO 13
<211> LENGTH: 214
<212> TYPE: PRT
<213> ORGANISM: Mus musculus
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 13

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
```

```
                  35                  40                  45
Tyr Tyr Ala Ser Asn Arg Tyr Thr Gly Val Pro Asp Arg Phe Thr Gly
 50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Trp
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
            210

<210> SEQ ID NO 14
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 14

Glu Ile Val Met Thr Gln Ser Pro Ala Thr Leu Ser Val Ser Pro Gly
 1               5                  10                  15

Glu Arg Ala Thr Leu Ser Cys Lys Ala Ser Gln Ser Val Ser Asn Asp
             20                  25                  30

Val Ala Trp Tyr Gln Gln Lys Pro Gly Lys Ala Pro Lys Leu Leu Ile
         35                  40                  45

Tyr Tyr Ala Ser Asn Arg Tyr Thr Gly Ile Pro Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Gln Gln Asp Tyr Ser Ser Pro Trp
                 85                  90                  95

Thr Phe Gly Gln Gly
            100
```

```
<210> SEQ ID NO 15
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
                20                  25                  30

Val Ala Trp Phe Gln Gln Arg Pro Gly Gln Ser Pro Arg Arg Leu Ile
            35                  40                  45

Tyr Tyr Ala Ser Asn Arg Tyr Thr Gly Val Pro Ser Arg Phe Ser Gly
 50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asp Tyr Ser Ser Pro Trp
                85                  90                  95

Thr Phe Gly Gln Gly
                100

<210> SEQ ID NO 16
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
                20                  25                  30

Val Ala Trp Tyr Gln Gln Lys Pro Gly Gln Ala Pro Arg Leu Leu Ile
            35                  40                  45

Tyr Tyr Ala Ser Asn Arg Tyr Thr Gly Ile Pro Pro Arg Phe Ser Gly
 50                  55                  60

Ser Gly Tyr Gly Thr Asp Phe Thr Leu Thr Ile Asn Asn Ile Glu Ser
65                  70                  75                  80
```

Glu Asp Ala Ala Tyr Tyr Phe Cys Gln Gln Asp Tyr Ser Ser Pro Trp
                85                  90                  95

Thr Phe Gly Gln Gly
            100

<210> SEQ ID NO 17
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Leu Gln Lys Pro Gly Gln Ser Pro Gln Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Asp Tyr Ser Ser Pro Trp
                85                  90                  95

Thr Phe Gly Gln Gly
            100

<210> SEQ ID NO 18
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 18

Asp Ile Val Met Thr Gln Thr Pro Leu Ser Leu Pro Val Thr Pro Gly
1               5                   10                  15

Glu Pro Ala Ser Ile Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

```
Tyr Tyr Ala Ser Asn Arg Tyr Thr Gly Ile Pro Pro Arg Phe Ser Gly
            50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Gln Gln Asp Tyr Ser Ser Pro Trp
                85                  90                  95

Thr Phe Gly Gln Gly
            100

<210> SEQ ID NO 19
<211> LENGTH: 101
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (27)..(32)
<223> OTHER INFORMATION: CDR according to IGMT
<220> FEATURE:
<221> NAME/KEY: MISC_FEATURE
<222> LOCATION: (50)..(52)
<223> OTHER INFORMATION: CDR according to IGMT
<220> FEATURE:
<221> NAME/KEY: MISC_FEATURE
<222> LOCATION: (89)..(97)
<223> OTHER INFORMATION: CDR according to IGMT

<400> SEQUENCE: 19

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
            50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Asp Tyr Ser Ser Pro Trp
                85                  90                  95

Thr Phe Gly Gln Gly
            100

<210> SEQ ID NO 20
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 20

Gln Val Gln Leu Val Gln Ser Gly Ala Glu Val Lys Lys Pro Gly Ala
```

```
                1               5                   10                  15
        Ser Val Lys Val Ser Cys Lys Ala Ser Gly Tyr Thr Phe Thr Ser Tyr
                        20                  25                  30

Asn Met His Trp Val Arg Gln Ala Thr Gly Gln Gly Leu Glu Trp Met
                        35                  40                  45

Gly Ala Ile Tyr Pro Gly Asn Gly Asp Thr Ser Tyr Asn Gln Lys Phe
                        50                  55                  60

Lys Gly Arg Val Thr Ile Thr Ala Asp Lys Ser Thr Ser Thr Ala Tyr
         65                  70                  75                  80

Met Glu Leu Ser Ser Leu Arg Ser Glu Asp Thr Ala Val Tyr Tyr Cys
                        85                  90                  95

Ala Arg Gly Gly Thr Gly Phe Ala Tyr Trp Gly Gln Gly
                        100                 105

<210> SEQ ID NO 21
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 21

Gln Val Gln Leu Gln Gln Ser Gly Pro Gly Leu Val Lys Pro Ser Gln
         1               5                   10                  15

Thr Leu Ser Leu Thr Cys Ala Ile Ser Gly Tyr Thr Phe Thr Ser Tyr
                        20                  25                  30

Asn Met His Trp Ile Arg Gln Pro Pro Gly Lys Gly Leu Glu Trp Ile
                        35                  40                  45

Gly Ala Ile Tyr Pro Gly Asn Gly Asp Thr Ser Tyr Asn Gln Lys Phe
                        50                  55                  60

Lys Gly Arg Val Thr Ile Thr Ala Asp Lys Ser Thr Ser Thr Ala Tyr
         65                  70                  75                  80

Met Glu Leu Ser Ser Leu Arg Ser Glu Asp Thr Ala Val Tyr Tyr Cys
                        85                  90                  95

Ala Arg Gly Gly Thr Gly Phe Ala Tyr Trp Gly Gln Gly
                        100                 105

<210> SEQ ID NO 22
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
```

-continued

```
<221> NAME/KEY: MISC_FEATURE
<222> LOCATION: (97)..(105)
<223> OTHER INFORMATION: CDR according to IGMT

<400> SEQUENCE: 22
```

Gln Val Gln Leu Gln Gln Ser Gly Pro Gly Leu Val Lys Pro Ser Gln
1               5                   10                  15

Thr Leu Ser Leu Thr Cys Ala Ile Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
50                  55                  60

Lys Gly Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
            85                  90                  95

Ala Arg Gly Gly Thr Gly Phe Ala Tyr Trp Gly Gln Gly
            100                 105

```
<210> SEQ ID NO 23
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 23
```

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
50                  55                  60

Lys Gly Arg Phe Thr Ile Ser Arg Asp Asp Ser Lys Asn Thr Ala Tyr
65                  70                  75                  80

Leu Gln Met Asn Ser Leu Lys Thr Glu Asp Thr Ala Val Tyr Tyr Cys
            85                  90                  95

Ala Arg Gly Gly Thr Gly Phe Ala Tyr Trp Gly Gln Gly
            100                 105

```
<210> SEQ ID NO 24
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
```

```
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 24

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Thr Gly Phe Ala Tyr Trp Gly Gln Gly
            100                 105

<210> SEQ ID NO 25
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Phe Ala Tyr Trp Gly Gln Gly
            100                 105

<210> SEQ ID NO 26
```

```
<211> LENGTH: 109
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 26

Gln Val Gln Leu Gln Gln Ser Gly Pro Gly Leu Val Lys Pro Ser Gln
1               5                   10                  15

Thr Leu Ser Leu Thr Cys Ala Ile Ser Gly Tyr Thr Phe Thr Ser Tyr
            20                  25                  30

Asn Met His Trp Val Arg Gln Ala Thr Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Gly Phe Ala Tyr Trp Gly Gln Gly
            100                 105

<210> SEQ ID NO 27
<211> LENGTH: 108
<212> TYPE: PRT
<213> ORGANISM: Artificial Sequence
<220> FEATURE:
<223> OTHER INFORMATION: humanized variant
<220> FEATURE:
<221> NAME/KEY: MISC_FEATURE
<222> LOCATION: (26)..(33)
<223> OTHER INFORMATION: CDR according to IGMT
<220> FEATURE:
<221> NAME/KEY: MISC_FEATURE
<222> LOCATION: (51)..(58)
<223> OTHER INFORMATION: CDR according to IGMT
<220> FEATURE:
<221> NAME/KEY: MISC_FEATURE
<222> LOCATION: (97)..(105)
<223> OTHER INFORMATION: CDR according to IGMT

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Ala Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                85                  90                  95

Ala Arg Gly Gly Thr Gly Phe Ala Tyr Trp Gly Gln
            100                 105

<210> SEQ ID NO 28
<211> LENGTH: 5
<212> TYPE: PRT
<213> ORGANISM: Mus musculus

<400> SEQUENCE: 28

Ser Tyr Asn Met His
1               5

<210> SEQ ID NO 29
<211> LENGTH: 17
<212> TYPE: PRT
<213> ORGANISM: Mus musculus

<400> SEQUENCE: 29

Ala Ile Tyr Pro Gly Asn Gly Asp Thr Ser Tyr Asn Gln Lys Phe Lys
1               5                   10                  15

Gly

<210> SEQ ID NO 30
<211> LENGTH: 7
<212> TYPE: PRT
<213> ORGANISM: Mus musculus

<400> SEQUENCE: 30

Gly Gly Thr Gly Phe Ala Tyr
1               5

<210> SEQ ID NO 31
<211> LENGTH: 11
<212> TYPE: PRT
<213> ORGANISM: Mus musculus

<400> SEQUENCE: 31

Lys Ala Ser Gln Ser Val Ser Asn Asp Val Ala
1               5                   10

<210> SEQ ID NO 32
<211> LENGTH: 7
<212> TYPE: PRT
<213> ORGANISM: Mus musculus

<400> SEQUENCE: 32

Tyr Ala Ser Asn Arg Tyr Thr
1               5

<210> SEQ ID NO 33
<211> LENGTH: 25
<212> TYPE: DNA
<213> ORGANISM: Artificial Sequence
<220> FEATURE:
<223> OTHER INFORMATION: forward primer for PCR of human netrin-1 gene

<400> SEQUENCE: 33
aaaagtactg caagaaggac tatgc                                       25

<210> SEQ ID NO 34
<211> LENGTH: 21
<212> TYPE: DNA
<213> ORGANISM: Artificial Sequence
```

```
<220> FEATURE:
<223> OTHER INFORMATION: reverse primer for PCR of human netrin-1 gene

<400> SEQUENCE: 34
ccctgcttat acacggagat g                                        21

<210> SEQ ID NO 35
<211> LENGTH: 22
<212> TYPE: PRT
<213> ORGANISM: Homo sapiens

<400> SEQUENCE: 35

Ala Arg Arg Cys Arg Phe Asn Met Glu Leu Tyr Lys Leu Ser Gly Arg
1               5                   10                  15

Lys Ser Gly Gly Val Cys
            20

<210> SEQ ID NO 36
<211> LENGTH: 66
<212> TYPE: DNA
<213> ORGANISM: Artifcial Sequence
<220> FEATURE:
<223> OTHER INFORMATION: NTN1 epitopic cDNA sequence

<400> SEQUENCE: 36
gcccggcgct gccgcttcaa catggagctc tacaagcttt cggggcgcaa gagcggaggt    60
gtctgc                                                               66
```

COMBINED TREATMENT WITH NETRIN-1 INTERFERING DRUG AND IMMUNE CHECKPOINT INHIBITORS DRUGS

The present invention relates to novel combined compositions and methods to treat cancer.

BACKGROUND

The axon guidance protein Netrin-1 is a soluble protein, proposed to play a crucial role in cancer progression by regulating programmed cell death.

Indeed, Netrin-1 receptors like DCC and UNC5H (i.e., UNC5H1, UNC5H2, UNC5H3 and UNC5H4 also called UNC5A, UNC5B, UNC5C or UNC5D)—belong to the so-called dependence receptor family. These transmembrane receptors act on two opposite manners: they induce a positive signalling leading to cell proliferation, survival and differentiation in presence of their ligand Netrin-1. In absence of Netrin-1, these receptors transduce a negative signalling triggering apoptosis when unbound. The signalling pathway of cell death induction upon ligand withdrawal required interaction and cleavage by specific apical caspases. As a consequence, mutation of caspase site in intracellular part of the receptor prevents cell death induction, observed in absence of Netrin-1. Thus, a single point mutation on the aspartic acid-1290 (D1290) residue is sufficient to inhibit DCC induce cell death, without interfering with DCC positive signaling. Mice bearing this mutation spontaneously develop intestinal neoplasia at relatively low level. When crossed in an $APC^{1638N}$ background they display an increase in tumor incidence.

Properties of dependence receptor to induce apoptosis confer them tumor suppressor activities. They are able to eliminate cells that abnormally grow in area offering a limited amount of Netrin-1. In the model of dependence receptors, a transformed cell submitted to an environment limited in ligand concentration or metastatic cells migrating to distant sites in which ligand is absent would display unbound dependence receptors and therefore undergo apoptosis. This mechanism would represent an alternative limitation for tumorigenesis. In aggressive tumors, tumor cells have shut down dependence receptors induced cell death. In agreement with this hypothesis, a loss of receptor expression represents a selective advantage for tumor cells and seem to be a primary method to surmount this safeguard mechanism. Numerous molecular mechanisms leading to dependence receptor loss of expression in cancer have been related. Dependence receptors expression has been related to be silence by loss of heterozygocity (LOH), by hyper-methylation or epigenetic mechanism, post-translational modification such as microRNAs and missense mutations. Thus, DCC gene is functionally silenced by LOH in 70% of human colorectal carcinoma. The expression of UNCH5 family receptors appears down-regulated in various cancers in many cases due to promoter methylation or mutations.

As dependence receptors induce cell death in area lacking of ligand, an additional mechanism for tumor escape is the autocrine synthesis of Netrin-1 by tumor cells. Thus, expression of Netrin-1 has been related to be increase in a large fraction of tumor types such as ovary, neuroblastoma, B-cell lymphomas, Non-small cell lung cancer, medulloblastoma, in inflammatory associated colorectal cancer. Additionally, Netrin-1 over-expression is correlated with metastatic and aggressive forms of breast cancer.

Proof-of concept studies to characterize as a therapeutic target has been performed in vivo. Consequently, silencing of Netrin-1 by siRNA or interference with Netrin-1/dependence receptors interaction are concomitant with tumor cell apoptosis. An anti-Netrin-1 monoclonal antibody (HUM03) has been characterized and shown to be effective in classic proliferative tumor growth models in immuno-compromised mice (Grandin et al., Cancer Cell, 2016 and WO2015/104360). This antibody is able to disrupt Netrin-1/Dependence receptors interaction or netrin-1 mediated netrin-1 receptors dimerization.

Moreover, netrin-1 has been recently identified as a regulator of immune cell migration and has led to a large number of studies looking into how netrin-1 controls inflammation and inflammatory cell migration, in several pathologies such as: acute and chronic kidney disease, inflammatory arthritis, atherosclerosis or diabetes/obesity. Netrin-1 was shown to promote inflammation arthritis, atherosclerosis or obesity by preventing macrophage egress from inflamed sites, from plaques of the artery wall, or by accumulating these cells in adipose tissue, thus promoting chronic inflammation and insulin resistance. Thus, it seems that netrin-1 regulates inflammation but the mechanism by which this occurs is unknown.

Immunotherapy is a current revolution in the field of cancer treatment with the clear-cut long-lasting response observed in patients treated with the immune checkpoints inhibitors, notably monoclonal antibodies directed against PD1/PDL1 or CTLA4.

CTLA4 (cytotoxic T-lymphocyte-associated protein 4, also known as CD152 (cluster of differentiation 152)), is a protein receptor that, acting as an immune checkpoint, down-regulates immune responses. CTLA4 is constitutively expressed in T-lymphocyte-regulators (Tregs) but only upregulated in conventional T-lymphocyte after activation. It acts as an "off" switch when bound to CD80 or CD86 at cell surface of antigen-presenting cells (APC). The PD-1 (programmed cell death-1) receptor (also known as CD279) is expressed on the surface of activated T cells. Its ligands, PD-L1 (B7-H1; CD274) and PD-L2 (B7-DC; CD273) are commonly expressed at surface of macrophages or dendritic cells. PD1 and PD-L1/PD-L2 belong to the family of immune checkpoint proteins that act as co-inhibitory factor, which can stop or limit the development of the T cell response. PD1/PD-L1 interaction ensures that the immune system is activated only at the appropriate time in order to reduce the possibility of prolonged autoimmune inflammation.

When PD-1 binds to PD-L1, a negative signaling is transmitted in T cell, which reduces cytokine production and suppresses T-cell proliferation. Tumor cells avoid this pathway as a mechanism to evade detection and prevent immune response. PD-L1 is described to be over-expressed by tumor cells or by microenvironment. PD-L1 expressed on the tumor cells binds to PD-1 receptors on the activated T cells, which leads to the inhibition of the cytotoxic T cells. These deactivated T cells remain inhibited in the tumor microenvironment. The PD1/PD-L1 pathway represents an adaptive immune resistance mechanism that is exerted by tumor cells in response to endogenous anti-tumor activity. Cancer immunotherapy research is trying to overcome the cancer's ability to block the immune responses and to stimulate the body's own mechanisms to remain effective against cancer.

However, two major limits have been reported:
The main limit is the efficacy of the compounds, as only a fraction of patients show a response to these immune checkpoint inhibitors (may not respond to an immune check point inhibitor). Thus, only 50% of patients with melanoma exhibit objective responses to combination blockade of CTLA4 and PD1, and this percentage drops to ~20% in non-small cell lung cancer and <5% in breast or colon cancer.

The second limit is that so far it is not possible to predict whether a patient is going to positively respond or not. The abundance of immune effectors (and in particular CD8+ cytotoxic T lymphocytes, CTL) combined with a scarcity of immunosuppressive cells (in particular FOXP3+ regulatory T cells, Tregs) in the tumor bed is an important, yet imperfect prognostic factor. Different reports have suggested that chemotherapies may potentiate the effect of immune-oncology drugs, notably because some cytotoxic agents can stimulate immunogenic cell death (ICD) of malignant cells, hence favoring their immune recognition. Whether cell death induced by netrin-1 interference is immunogenic is not known so far. Moreover even though netrin-1 has been shown to act as a survival factor in cancer progression, in non-cancer settings, it has recently been shown that netrin-1 can act as an immune guidance cue for T cells or Macrophage even though conflicting data have been described (Ramkhelawon et al., Nature Med, 2013: Boneschansker et al., J. Immunology, 2016). Different chemokines produced by tumor tissue such as CXCL12 are known to recruit immunosuppressive cells such as Treg and myeloid-derived immunosuppressor cells. These cells release different mediators that impair the function of cytotoxic T-cells and dendritic cells, such as TGF-Beta (Transforming growth factor-beta), IL10 (interleukine-10) and VEGF (Vascular endothelial growth factor), generating an immuno-tolerant microenvironment. All these secreted proteins have been described to be related to netrin-1. Indeed, it has been shown that (i) netrin-1 specifically promotes the chemotaxis of CXCL12, (ii) IL-10 facilitates neurite outgrowth by increasing the expression of netrin-1, (iii) there is a link between TGF-Beta and netrin-1 and (iv) there is a link between VEGF and netrin-1 as netrin-1 stimulates angiogenesis in vivo and augments the response to vascular endothelial growth factor.

SUMMARY OF INVENTION

The effect of drug combination is inherently unpredictable. There is often a propensity for one drug to partially or completely inhibit the effects of the other. The present invention is based on the surprising observation of a significant increase of xenografted mice survival and longer disease control by combination therapy using an anti-netrin-1 antibody HUM03 and a monoclonal antibody against CTLA4 or PD-1. The data obtained support the view that combining a monoclonal antibody directed against netrin-1 to the current immunotherapeutic treatments is boosting their efficacy. In a search of the mechanism that may explain this enhanced effect of immune checkpoint inhibitors in presence of netrin-1 interference, we analyse the tumor immune infiltrate in response to monotherapy or combination treatment. As presented in FIG. 5, while the monotherapy (either HUM03 or CTLA4) is not affecting significantly the ratio T cell effector/T cell regulator, the combination is shifting the ratio toward T cell effector. This supports the increased efficacy by suggesting that the combination is enhancing the presence of the killer lymphoid cells (T cell effector).

An object of the invention is the combination or combined use of (i) a compound able to disrupt or impede netrin-1/netrin-1 receptors interaction or netrin-1-mediated receptor dimerization, also called herein a NTN1 neutralizing agent, which compound may be an antibody binding to netrin-1 or anti-netrin-1 antibody, and (ii) an immune checkpoint inhibitor, in the treatment of cancer.

Another object of the invention is the combination or combined use of an antibody binding to netrin-1 or anti-netrin-1 antibody and an immune checkpoint inhibitor, in the treatment of cancer.

Another object of the invention is a composition comprising (i) a compound able to disrupt or impede netrin-1/netrin-1 receptors interaction or netrin-1-mediated receptor dimerization, which compound may be an antibody binding to netrin-1 or anti-netrin-1 antibody, and (ii) an immune checkpoint inhibitor, for use as an anticancerous drug with a simultaneous, separate or sequential administration of the compound (i) and the immune checkpoint inhibitor (ii) to a patient.

Another object of the invention is a composition comprising (i) an antibody binding to netrin-1 or anti-netrin-1 antibody and (ii) an immune checkpoint inhibitor, for use as an anticancerous drug with a simultaneous, separate or sequential administration of the anti-netrin-1 antibody and the immune checkpoint inhibitor to a patient.

Another object of the present invention is also a method of combined anti-cancer treatment comprising the administration to a patient of (i) a compound able to disrupt or impede netrin-1/netrin-1 receptors interaction or netrin-1-mediated receptor dimerization, which compound may be an antibody binding to netrin-1 or anti-netrin-1 antibody, and (ii) an immune checkpoint inhibitor.

Another object of the present invention is also a method of combined anti-cancer treatment comprising the administration to a patient of (i) an antibody binding to netrin-1 or anti-netrin-1 antibody and (ii) an immune checkpoint inhibitor.

Another object of the present invention is a method to modulate tumor infiltrate (i.e. Lymphocyte T or B, macrophages, natural killers cells) in vivo, comprising the administration to a patient of (i) a compound able to disrupt or impede netrin-1/netrin-1 receptors interaction or netrin-1-mediated receptor dimerization, which compound may be an antibody binding to netrin-1 or anti-netrin-1 antibody, and (ii) an immune checkpoint inhibitor.

Another object of the present invention is a method to modulate tumor infiltrate (i.e. Lymphocyte T or B, macrophages, natural killers cells) in vivo, comprising the administration to a patient of (i) an antibody binding to netrin-1 or anti-netrin-1 antibody, and (ii) an immune checkpoint inhibitor.

Another object is the activation immune response by activating cancer cell death or immunogenic cell death, comprising the administration to a patient of (i) a compound able to disrupt or impede netrin-1/netrin-1 receptors interaction or netrin-1-mediated receptor dimerization, which compound may be an antibody binding to netrin-1 or anti-netrin-1 antibody, and (ii) an immune checkpoint inhibitor.

Another object is the activation immune response by activating cancer cell death or immunogenic cell death, comprising the administration to a patient of (i) an antibody binding to netrin-1 or anti-netrin-1 antibody, and (ii) an immune checkpoint inhibitor.

Other specific objects of the invention are:
  a pharmaceutical composition comprising an anti-netrin-1 antibody and an immune checkpoint inhibitor, wherein the anti-netrin-1 antibody is able to disrupt or impede netrin-1/netrin-1 receptors interaction or netrin-1-mediated receptor dimerization, for use in a method for the treatment of a cancer;

a pharmaceutical composition comprising an anti-netrin-1 antibody and an immune checkpoint inhibitor, wherein the anti-netrin-1 antibody specifically binds to a polypeptide of amino acid sequence SEQ ID NO: 35, and is able to disrupt or impede netrin-1/netrin-1 receptors interaction or netrin-1-mediated receptor dimerization;

a pharmaceutical composition comprising an anti-netrin-1 antibody and an immune checkpoint inhibitor, wherein the anti-netrin-1 antibody comprises (i) a CDR1-H of sequence SEQ ID NO: 5, a CDR2-H of sequence SEQ ID NO: 6, a CDR3-H of sequence SEQ ID NO: 7, and a CDR1-L of sequence SEQ ID NO: 8, a CDR2-L of sequence YAS and a CDR3-L of sequence SEQ ID NO: 9, or (ii) a CDR1-H of sequence SEQ ID NO: 28, a CDR2-H of sequence SEQ ID NO: 29, a CDR3-H of sequence SEQ ID NO: 30, and a CDR1-L of sequence SEQ ID NO: 31, a CDR2-L of sequence SEQ ID NO: 32 and a CDR3-L of sequence SEQ ID NO: 9;

a pharmaceutical composition comprising an anti-netrin-1 antibody and an immune checkpoint inhibitor, wherein the anti-netrin-1 antibody is able to disrupt or impede netrin-1/netrin-1 receptors interaction or netrin-1-mediated receptor dimerization, and the immune checkpoint inhibitor is selected from the group consisting of anti-PD1, anti-PD-L1, anti-PD-L2 and anti-CTLA-4 antibodies;

a method of anti-cancer treatment comprising the administration to a patient in need thereof of an efficient amount of an anti-netrin-1 antibody and of an immune checkpoint inhibitor, wherein the anti-netrin-1 antibody is able to disrupt or impede netrin-1/netrin-1 receptors interaction or netrin-1-mediated receptor dimerization.

In an embodiment, the cancers to be treated are cancers with netrin-1 expression and that may not respond to an immune check point inhibitor (alone, i.e. if not combined to the anti-netrin-1 antibody and the like).

These different objects may in particular be made using the HUM03 antibody or one of its parent antibodies, as it will be presented thereafter.

In these different objects of the invention the immune checkpoint inhibitor may be or comprise particularly an antibody, preferably a monoclonal antibody.

DETAILED DESCRIPTION

The NTN1 (Netrin-1) Neutralizing Agent

The NTN1 neutralizing agent is a drug which interferes with the netrin-1 ability to interact with a netrin-1 receptor, or which interferes with the ability of netrin-1 to induce dimerization or multimerization of netrin-1 receptor. It is called herein a compound able to disrupt or impede netrin-1 and dependence receptor interaction or dependence receptor dimerization. The person skilled in the art may refer to WO2007/099133, incorporated herein by reference, which discloses interference between netrin-1 and its receptors, either a decrease or an inhibition of interaction or binding between netrin-1 and receptors, or a decrease or an inhibition of the ability of netrin-1 to induce dimerization or multimerization (we simply refer herein to dimerization, which may encompass multimerization) of netrin-1 receptor, whereby netrin-1 receptors-induced apoptosis is promoted.

In an embodiment, the NTN1 neutralizing agent is a small interfering RNA or siRNA which is a double stranded RNA (dsRNA) (that may have namely from 10 to 50 nucleotides in length) and which reduces expression of the gene coding for netrin-1. Portions of the first strand are complementary to the target gene, i.e. it has sufficient complementarity to hybridize to the target gene. For example there is at least 80% identity to the target gene or to a portion thereof. AP: human Netrin-1 mRNA sequence accession number: NM_004822. siRNA sequence that may be used: amino acids 94-114 of sequence NM_004822.

In a second embodiment, the NTN1 neutralizing agent is a molecule (e.g. antibody, polypeptide, small molecule, and the like) which binds to netrin-1 and netrin-1 is rendered unable to bind to its receptors or to induce dimerization/multimerization of the netrin-1 receptors, especially DCC and/or UNC5.

In a third embodiment, the NTN1 neutralizing agent is a molecule (e.g. antibody, polypeptide, small molecule, and the like) which binds to a netrin-1 receptor, this binding inhibiting NTN1 binding to receptor or dimerization/multimerization of the receptor.

The NTN1 neutralizing agent may induce NTN1 receptor-mediated apoptosis.

The netrin-1 receptors may be in particular DCC, UNC5A, UNC5B, UNC5C or UNC5D, neogenin and A2b.

In a preferred embodiment, the NTN1 neutralizing agent is an antibody binding to netrin-1.

Anti-NTN1 Antibodies (Anti-Netrin-1 Antibody or Antibody Binding to Netrin-1)

It is preferably a polyclonal or monoclonal antibody specifically binding to netrin-1. The antibody is preferably able to disrupt or impede netrin-1/netrin-1 receptors interaction or netrin-1-mediated receptor dimerization (i.e., netrin-1 receptors including UNC5B, A, C, D, DCC, neogenin, and A2b).

A NTN1 polyclonal antibody may, inter alia, be obtained by immunizing an animal such as a rabbit, a mouse and the like with the aid of the selected amino acid sequence, collecting and then depleting the antiserum obtained on, for example, an immunoadsorbent containing the receptor according to methods known per se to a person skilled in the art.

The netrin-1 amino acid sequence is as depicted on SEQ ID NO: 1 and netrin-1 may be used in whole or in part to design antibodies.

Generally, monoclonal antibodies may be obtained according to the conventional method of lymphocyte fusion and hybridoma culture described by Köhler and Milstein, (Nature, 1975, 256(5517): 495-7). Other methods for preparing monoclonal antibodies are also known (Harlow et al., ed., 1988 "Antibodies: a laboratory manual"). The monoclonal antibodies may be prepared by immunizing a mammal (for example a mouse, a rat, a rabbit or even a human being, and the like) and using the lymphocyte fusion technique leading to hybridoma (Köhler and Milstein, 1975). Alternative techniques to this customary technique exist. It is possible, for example, to produce monoclonal antibodies by expressing a nucleic acid cloned from a hybridoma. It is also possible to produce antibodies by the phage display technique by introducing cDNAs for antibodies into vectors, which are typically filamentous phages which exhibit gene libraries V at the surface of the phage (for example fUSE5 for *E. coli*, Scott J. K., Smith G. P. Science 1990; 249:386-390). Protocols for constructing these antibody libraries are described in J. D. Marks et al., J. Mol. Biol., 222 (1991), p. 581). The cDNA corresponding to full length netrin-1 with signal sequence (SEQ ID NO: 2) or to a suitable fragment thereof may be used to produce monoclonal antibodies according to these methods.

In a preferred embodiment, the NTN1 neutralizing antibody is one disclosed in WO2015/104360, which reference is incorporated herein by reference. It is an antibody that specifically binds to a NTN1 epitope or polypeptide having the amino acid sequence SEQ ID NO: 3 or 35 or a variant thereof. These antibodies have the property of binding to NTN1 and induce cell death or apoptosis of a tumor cell via a netrin-1 receptor, such as an UNC5 or DCC receptor. These antibodies are preferably monoclonal antibodies. These antibodies are able to disrupt or impede netrin-1/netrin-1 receptors interaction or netrin-1 mediated-dimerization. Various derivable forms of antibodies (including fragments and combination thereof) will be described later herein.

In an embodiment, based on an IMGT CDR's definition, the antibody comprises a CDR1-H of sequence SEQ ID NO: 5, a CDR2-H of sequence SEQ ID NO: 6, a CDR3-H of sequence SEQ ID NO: 7, a CDR1-L of sequence SEQ ID NO: 8, a CDR2-L of sequence YAS and a CDR3-L of sequence SEQ ID NO: 9. Based on a Kabat CDR's definition, the antibody comprises a CDR1-H of sequence SEQ ID NO: 28, a CDR2-H of sequence SEQ ID NO: 29, a CDR3-H of sequence SEQ ID NO: 30, a CDR1-L of sequence SEQ ID NO: 31, a CDR2-L of sequence SEQ ID NO:32 and a CDR3-L of sequence SEQ ID NO: 9.

In a first series of embodiments, the antibody of the invention comprises an amino acid sequence SEQ ID NO: 10, 11, 12 or 13. Typically, it comprises both sequences SEQ ID NO: 10 and 11, or SEQ ID NO: 12 and 13.

In a second series of embodiments, the antibody is humanized. Preferably it comprises an amino acid sequence selected from the group of SEQ ID NO: 14 to 19 (VL) and/or from the group of SEQ ID NO: 20 to 27 (VH). Typically, the antibody is humanized and comprises an amino acid sequence selected from the group of SEQ ID NO: 14 to 19 and an amino acid sequence selected from the group of SEQ ID NO: 20 to 27.

Specific embodiments are the following humanized antibodies. The first listed in this table corresponds to the grafting of the murine CDRs into a human IgG1. The others called HUM are monoclonal antibodies having variable human framework regions. In an embodiment, the invention makes use of, or the compositions of the invention comprise, HUM01, HUM02, HUM03, HUM04, HUM05, HUM06, HUM07, HUM08, HUM09 and/or HUM10. In a typical embodiment, HUM03 is used. Table 1 gives also a reference for the CH and CL of a human IgG1:

TABLE 1

| | VH SEQ ID NO: | Constant heavy chain | VL SEQ ID NO: | Constant light chain |
|---|---|---|---|---|
| CDR graft (murine CDRs grafted into human IgG1 VH or VL) | 27 | Human IgG1 (GenBank: AEL33691.1 modified R97K) | 19 | Human IgG1 (GenBank: CAC20459.1) |
| HUM01 | 20 | Human IgG1 | 14 | Human IgG1 |
| HUM02 | 21 | Human IgG1 | 15 | Human IgG1 |
| HUM03 | 22 | Human IgG1 | 16 | Human IgG1 |
| HUM04 | 23 | Human IgG1 | 17 | Human IgG1 |
| HUM05 | 24 | Human IgG1 | 17 | Human IgG1 |
| HUM06 | 25 | Human IgG1 | 16 | Human IgG1 |
| HUM07 | 26 | Human IgG1 | 17 | Human IgG1 |
| HUM08 | 22 | Human IgG1 | 17 | Human IgG1 |
| HUM09 | 25 | Human IgG1 | 18 | Human IgG1 |
| HUM10 | 21 | Human IgG1 | 16 | Human IgG1 |

NTN1 Receptor Polypeptide

In another embodiment, the NTN1 (netrin-1) neutralizing agent drug is a compound comprising an extracellular domain of a netrin-1 receptor or a fragment of said extracellular domain. For example, the amino acid sequence of the extracellular domain of a netrin-1 receptor or a fragment of said extracellular domain are given in UniProt Sequence ID [extracellular domain position range]: UNC5A: Q6ZN44 [aas 26-306, or fragment 34-240]; UNC5B: Q8IZJ1 [aas 27-377 or fragment 29-244]; UNC5C: O95185 [aas 41-380 or fragment 61-258]; UNC5D: Q6UXZ4 [aas 33-379]; DCC: P43146 [aas 26-1097]. This drug is able to bind to netrin-1. The netrin-1 receptors may be DCC, UNC5A, UNC5B, UNC5C or UNC5D.

In an embodiment, the extracellular domain or part thereof is bound to an antibody Fc part. In a preferred embodiment, the Fc part is the Fc or part thereof of a human IgG. The human IgG may be namely IgG1, IgG2A, IgG2B, IgG3. In a preferred embodiment, the IgG is IgG1.

In an embodiment, the fusion protein is single chain, which means that the protein is made of a DCC or a UNC5 fragment comprising or constituted of respectively the fourth or fifth fibronectin-like domain of DCC or the two Ig-like domains of UNC5 and of a peptidic or protein sequence improving the pharmaceutical parameters of the compound.

In another preferred embodiment, the fusion protein is double chain, which means that the fusion protein is made of two chains each comprising or constituted of respectively the fourth or fifth fibronectin-like domain of DCC or the two Ig-like domains of UNC5 and of an antibody Fc part, wherein both chains are linked together, preferably by one or more, e.g. two, disulfide bonds.

In an embodiment, the drug comprises the fifth fibronectin domain (Fn5 or 5Fbn) of DCC. Preferably, the drug comprises a DCC-fusion protein comprising this Fn5 fused to an antibody Fc part. In a preferred embodiment, the Fc part is the Fc or part thereof of a human IgG. The human IgG may be namely IgG1, IgG2A, IgG2B, IgG3. In a preferred embodiment, the IgG is IgG1. The DCC gene is available for example from NCBI, under ID 1630 (as updated on Jul. 14, 2012), it encodes the DCC receptor protein as Uniprot P43146, updated Jul. 11, 2012. A DCC-fusion protein useful in the invention and comprising the Fn5 is described in WO2012025618, incorporated herein by reference. In an embodiment, the fusion protein has the amino acid sequence SEQ ID NO: 2, 3 or 4 in WO2012025618. In an embodiment, the fusion protein is encoded by the DNA sequence SEQ ID NO: 1 in WO2012025618. Other examples of fusion proteins comprising the Fn5 are the DCC-5-fibronectin fusion protein with Glutathione-S-transferase (DCC-5Fbn-GST) described in WO2007099133.

In an embodiment, the drug comprises the two Ig-like domains of a UNC5. Preferably, the drug comprises an UNC5-fusion protein comprising the two Ig-like domains of a UNC5 fused to an antibody Fc part. The human IgG may be namely IgG1, IgG2A, IgG2B, IgG3. In a preferred embodiment, the IgG is IgG1. In an embodiment, UNC5 is UNC5A. In another embodiment, UNC5 is UNC5B. In another embodiment, UNC5 is UNC5C. In still another embodiment, UNC5 is UNC5D.

In an embodiment, the UNC5A protein in UNC5A-fusion comprises or consists of the amino acids 20 to 217 of SEQ ID NO: 1 in WO2014/041088, which document is incorporated herein by reference. This fusion protein may further comprise the IgG1 Fc comprising or consisting of amino acids 220 to 446 of this SEQ ID NO: 1. This Fc is fused to the UNC5A protein, for example through a linker, such as GT. In an embodiment, the present invention relates to an UNC5A-fusion of UNC5A protein comprising or consisting of the amino acid sequence of this SEQ ID NO: 1: Kappa2 signal peptide sequence: aas 1 to 19; Ig-like domains of UNC5A: aas 20 to 217; Linker: aas 218-219; Human IgG1 Fc: aas 220 to 446. In an embodiment, the mature fusion protein does not comprise the Kappa2 signal peptide sequence. In a preferred embodiment, the fusion protein is double chain. The present invention also encompasses variant sequences having a percentage of identity which is equal or more than 90%, preferably than 96, 95, 94, 93, 92 or 91%, on the whole length of the 20-217 amino acid sequence, or of amino acids 20-446 of this SEQ ID NO: 1. Amino acid substitutions may for example occur at one or several of positions 9, 72, 74, 87, 144, 164, 170, 193 and/or 210 on the whole length of the 20-217 amino acid sequence, or of this SEQ ID NO: 1.

In another embodiment, the UNC5B protein in UNC5B-fusion comprises or consists of the amino acids 20 to 215 of SEQ ID NO: 2 in WO2014/041088. This fusion protein may further comprise the IgG1 Fc comprising or consisting of amino acids 218 to 444 of this SEQ ID NO: 2. This Fc is fused to the UNC5B protein, for example through a linker, such as GT. In an embodiment, the present invention relates to an UNC5B-fusion of UNC5B protein comprising or consisting of the amino acid sequence of this SEQ ID NO: 2: Kappa2 signal peptide sequence: aas 1 to 19; Ig-like domains of UNC5B: aas 20 to 215; Linker: aas 216-217; Human IgG1 Fc: aas 218 to 444. In an embodiment, the mature fusion protein does not comprise the Kappa2 signal peptide sequence. In a preferred embodiment, the fusion protein is double chain. The present invention encompasses variant sequences having a percentage of identity which is equal or more than 90%, preferably than 96, 95, 94, 93, 92 or 91%, on the whole length of the 20-215 amino acid sequence, or of amino acids 20-444 of this SEQ ID NO: 2. Amino acid substitutions may for example occur at one or several of positions 29, 74, 100, 109, 113, 146, 149, 155, 172, 184, 189, 201, 213 and/or 214 on the whole length of the 20-215 amino acid sequence, or of this SEQ ID NO: 2.

In still another embodiment, the UNC5C protein in UNC5C-fusion comprises or consists of the amino acids 20 to 217 of SEQ ID NO: 3 in WO2014/041088. This fusion protein may further comprise the IgG1 Fc comprising or consisting of amino acids 220 to 446 of this SEQ ID NO: 3. This Fc is fused to the UNC5C protein, for example through a linker, such as GT. In an embodiment, the present invention relates to an UNC5C-fusion of UNC5C protein comprising or consisting of the amino acid sequence of this SEQ ID NO: 3: Kappa2 signal peptide sequence: aas 1 to 19; Ig-like domains of UNC5C: aas 20 to 217; Linker: aas 218-219; Human IgG1 Fc: aas 220 to 446. In an embodiment, the mature fusion protein does not comprise the Kappa2 signal peptide sequence. In a preferred embodiment, the fusion protein is double chain. The present invention encompasses variant sequences having a percentage of identity which is equal or more than 90%, preferably than 96, 95, 94, 93, 92 or 91%, on the whole length of the 20-217 amino acid sequence, or of amino acids 20-446 of this SEQ ID NO: 3. Amino acid substitutions may for example occur at one or several of positions 33, 66, 109, 129, 136, 178, 189 and/or 211 on the whole length of the 20-217 amino acid sequence, or of this SEQ ID NO: 3.

In still another embodiment, the UNC5D protein in UNC5D-fusion comprises or consists of the amino acids 20 to 217 of SEQ ID NO: 4 in WO2014/041088. This fusion protein may further comprise the IgG1 Fc comprising or consisting of amino acids 220 to 446 of this SEQ ID NO: 4. This Fc is fused to the UNC5D protein, for example through a linker, such as GT. In an embodiment, the present invention relates to an UNC5D-fusion of UNC5D protein comprising or consisting of the amino acid sequence of this SEQ ID NO: 4: Kappa2 signal peptide sequence: aas 1 to 19; Ig-like domains of UNC5D: aas 20 to 217; Linker: aas 218-219; Human IgG1 Fc: aas 220 to 446. In an embodiment, the mature fusion protein does not comprise the Kappa2 signal peptide sequence. In a preferred embodiment, the fusion protein is double chain. The present invention encompasses variant sequences having a percentage of identity which is equal or more than 90%, preferably than 96, 95, 94, 93, 92 or 91%, on the whole length of the 20-217 amino acid sequence, or of amino acids 20-446 of this SEQ ID NO: 4. Amino acid substitutions may for example occur at one or several of positions 38, 79, 80, 115, 131, 178, 186, 201 and/or 212 on the whole length of the 20-217 amino acid sequence, or of this SEQ ID NO: 4.

The invention may provide for administration of a nucleic acid encoding those polypeptides, rather than the polypeptide itself. Vectors able to express the polypeptide in the patient may be used, as it is usual. The person skilled in the art may refer to WO2007/099133 and WO2014/041088 which describe vectors and methods of preparing vectors and their use, which can be used in carrying out the present invention.

Checkpoints Inhibitors

In one aspect, the immune checkpoint inhibitor is a biologic therapeutic or a small molecule. In another aspect, the checkpoint inhibitor is a monoclonal antibody, a humanized antibody, a fully human antibody, a fusion protein or a combination thereof. The antibody may be directed against any protein that is involved in the pathway, and more particularly against either the receptor or the ligand. As it is known, an immune check point inhibitor is able to restore the immune response to the cancer cells. In particular, the inhibitor disrupts or impedes, or inhibits, the interaction between interacting proteins, and to allow for immune response, in particular T cells killing the tumor cells. In a further aspect, the checkpoint inhibitor inhibits a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 or a combination thereof. In an additional aspect, the checkpoint inhibitor interacts with a ligand of a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK1, CHK2, A2aR, B-7 or a combination thereof.

Anti-PD1, Anti-PD-L1 and Anti-PD-L2 Antibodies

Invention makes use of antibodies that blocks, inhibits or reduces the PD1/PD-L1 and/or PD1/PD-L2 pathway.

There are currently at least five agents blocking the pathway that are marketed or in clinical evaluation, any of these may be useful in combination with the invention. These agents are BMS-936558 (anti-PD-L1 mAb, Nivolumab/ONO-4538, Bristol-Myers Squibb, formerly MDX-1106 (antibody 5C4 in WO 2006/121168), MK-3475 (anti-PD1 mAb, lambrolizumab or pembrolizumab, Keytruda®, Merck), MPDL3280A/RG7446 (anti-PD-L1 mAb, Roche/Genentech), AMP-224 (immunoadhesin comprising an anti-PD-L2, Amplimmune and GSK), Pidlizumab (anti-PD1 mAb, CT-011, CureTech/TEVA—WO 2009/101611).

For MK-3475 DNA constructs encoding the variable regions of the heavy and light chains of the humanized antibodies h409All have been deposited with the American Type Culture Collection Patent Depository (10801 University Bld., Manassas, VA). The plasmid containing the DNA encoding the heavy chain of h409A-I 1 was deposited on Jun. 9, 2008, and identified as 081469_SPD-H and the plasmid containing the DNA encoding the light chain of h409Al 1 was deposited on Jun. 9, 2008 and identified as 0801470_SPD-L-I 1.

Further known PD-1 antibodies and other PD-1 inhibitors include AMP-224 (a B7-DC/IgG1 fusion protein licensed to GSK), AMP-514 described in WO 2012/145493, antibody MEDI-4736 (an anti-PD-L-1 developed by AstraZeneca/ Medimmune) described in WO2011/066389 and US2013/ 034559, antibody YW243.55.S70 (an anti-PD-L1) described in WO2010/077634, MDX-1105, also known as BMS-936559, is an anti-PD-L1 antibody developed by Bristol-Myers Squibb described in WO2007/005874, and antibodies and inhibitors described in WO2006/121168, WO2009/ 014708, WO2009/114335 and WO2013/019906. The disclosures of any document referred to herein are hereby incorporated by reference. Further examples of anti-PD1 antibodies are disclosed in WO2015/085847 for examples antibodies having light chain variable domain CDR1, 2 and 3 of SEQ ID NO:6, SEQ ID NO: 7 and SEQ ID NO: 8, respectively, and antibody heavy chain variable domain CDR1, 2 and 3 of SEQ ID NO: 3, SEQ ID NO: 4 and SEQ ID NO: 5, respectively, wherein the SEQ ID NO references are the numbering according to WO2015/085847.

Anti-CTLA-4 Antibodies

CTLA-4 (cytotoxic T-lymphocyte-associated protein 4), also known as CD152 is another inhibitor member of the CD28 family of receptors, and is expressed on T cells. Antibodies that bind and inhibit CTLA-4 are known in the art.

In one example, the antibody is ipilimumab (trade name Yervoy®, Bristol-Myers Squibb), a human IgG antibody.

Each one of these immune check point inhibitors, especially each one of these antibodies against PD1, PD-L1 or 2 or against CTLA-4 or natural binding partner or ligand, may be combined or used with one of the monoclonal antibodies disclosed herein in table 1, especially HUM01, HUM02, HUM03, HUM04, HUM05, HUM06, HUM07, HUM08, HUM09 and/or HUM10. In an embodiment, combination or use is with HUM03.

Definitions and Further Embodiments, Variants and Alternatives of the Invention

As used herein, a sequence "at least 85% identical to a reference sequence" is a sequence having, on its entire length, 85%, or more, in particular 90%, 91%, 92%, 93%, 94%, 95%, 96%, 97%, 98%, 99%, 99.5%, 99.6%, 99.7%, 99.8%, 99.9% or 100% sequence identity with the entire length of the reference sequence.

A percentage of "sequence identity" may be determined by comparing the two sequences, optimally aligned over a comparison window, wherein the portion of the polypeptide sequence in the comparison window may comprise additions or deletions (i.e. gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison is conducted by global pairwise alignment, e.g. using the algorithm of Needleman and Wunsch (1970) *J. Mol. Biol.* 48: 443. The percentage of sequence identity can be readily determined for instance using the program Needle, with the BLOSUM62 matrix, and the following parameters gap-open=10, gap-extend=0.5.

In the context of the invention, a "conservative amino acid substitution" is one in which an amino acid residue is substituted by another amino acid residue having a side chain group with similar chemical properties (e.g., charge or hydrophobicity). In general, a conservative amino acid substitution will not substantially change the functional properties of a protein. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine-tryptophan, lysine-arginine, alanine-valine, glutamate-aspartate, and asparagine-glutamine.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

An "antibody" may be a natural or conventional antibody in which two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site.

"Complementarity Determining Regions" or "CDRs" refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, in particular 90%, 95%, 97%, 99% or 100%) to the framework region of a naturally occurring human antibody.

In the context of the invention, CDR/FR definition in an immunoglobulin light or heavy chain is to be determined based on IMGT definition (Lefranc et al. (2003) Dev Comp Immunol. 27(1):55-77; world wide web.imgt.org).

As used herein, the term "antibody" denotes conventional antibodies and fragments thereof, as well as single domain antibodies and fragments thereof, in particular variable heavy chain of single domain antibodies, and chimeric, humanized, bispecific or multispecific antibodies.

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains. In particular, Camelidae species, for example camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody". Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard (2007) Appl. Microbiol. Biotechnol. 77:13-22.

The term "monoclonal antibody" or "mAb" as used herein refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e. produced by protein engineering.

"Fragments" of (conventional) antibodies comprise a portion of an intact antibody, in particular the antigen binding region or variable region of the intact antibody. Examples of antibody fragments include Fv, Fab, F(ab')$_2$, Fab', dsFv, (dsFv)$_2$, scFv, sc(Fv)$_2$, diabodies, bispecific and multispecific antibodies formed from antibody fragments. A fragment of a conventional antibody may also be a single domain antibody, such as a heavy chain antibody or VHH.

The term "Fab" denotes an antibody fragment having a molecular weight of about 50,000 Da and antigen binding activity, in which about a half of the N-terminal side of H chain and the entire L chain, among fragments obtained by treating IgG with a protease, papain, are bound together through a disulfide bond.

The term "F(ab')$_2$" refers to an antibody fragment having a molecular weight of about 100,000 Da and antigen binding activity, which is slightly larger than the Fab bound via a disulfide bond of the hinge region, among fragments obtained by treating IgG with a protease, pepsin.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv)$_2$.

"dsFv" is a VH::VL heterodimer stabilized by a disulphide bond. "(dsFv)$_2$" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

In a particular embodiment, the epitope-binding fragment is selected from the group consisting of Fv, Fab, F(ab')$_2$, Fab', dsFv, (dsFv)$_2$, scFv, sc(Fv)$_2$, diabodies and VHH.

A "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass.

The term "humanized antibody" refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin. As used herein, the term "humanized antibody" refers to a chimeric antibody which contain minimal sequence derived from non-human immunoglobulin, e.g. the CDRs.

The term "antibody" is used to encompass all these kinds of antibodies, fragments or combination thereof.

The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Antibodies can be humanized using a variety of other techniques including CDR-grafting (EP0239400; WO91/09967; U.S. Pat. Nos. 5,530,101 and 5,585,089), veneering or resurfacing (EP0592106; EP0519596; Padlan (1991) *Molecular Immunology* 28(415):489-498; Studnicka et al. (1994) *Protein Engineering* 7(6):805-814; Roguska et al. (1994) *Proc. Natl. Acad. Sci U.S.A.* 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and International patent application WO98/46645, WO98/50433, WO98/24893, WO98/16654, WO96/34096, WO96/33735, and WO91/10741.

In the context of the invention, the term "treating" or "treatment", as used herein, means reversing, alleviating, inhibiting the progress of, or preventing the disorder or condition to which such term applies, or one or more symptoms of such disorder or condition.

By the term "treating cancer" as used herein is meant in particular the inhibition of the growth of malignant cells of a tumour and/or the progression of metastases from said tumor. Such treatment can also lead to the regression of tumor growth, i.e., the decrease in size of a measurable tumor. In a particular embodiment, such treatment leads to a partial regression of the tumor or metastasis. In another particular embodiment, such treatment leads to the complete regression of the tumor or metastasis. In some aspect, treatment prevents metastasis.

According to the invention, the term "patient" or "patient in need thereof" is intended for a human or non-human mammal affected or likely to be affected with a malignant tumor.

By a "therapeutically effective amount" is meant a sufficient amount of the active agents to treat said cancer disease, at a reasonable benefit/risk ratio applicable to any medical treatment. It will be understood, however, that the total daily usage of the active agents will be decided by the attending physician within the scope of sound medical judgment. The specific therapeutically effective dose level for any particular patient will depend upon a variety of factors including the disorder being treated and the severity of the disorder; activity of the specific polypeptide or antibody employed; the specific composition employed, the age, body weight, general health, sex and diet of the patient; the time of administration, route of administration, and rate of excretion of the specific active agents employed; the duration of the treatment; drugs used in combination or coincidental with the specific active agents employed; and like factors well known in the medical arts.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Pharmaceutical Compositions:

The form of the pharmaceutical compositions including the polypeptide or antibody of the invention and the route of administration naturally depend upon the condition to be treated, the severity of the illness, the age, weight, and gender of the patient, etc.

The active agents of the invention can be formulated for a topical, oral, parenteral, intranasal, intravenous, intramuscular, subcutaneous or intraocular administration and the like. In a particular embodiment, the active agents of the invention are administered intravenously In particular, the pharmaceutical compositions including the active agents of the invention may contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

To prepare pharmaceutical compositions, an effective amount of the active agents of the invention may be dissolved or dispersed in a pharmaceutically acceptable carrier or aqueous medium.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

The carrier can be a solvent or dispersion medium containing, for example, water, ethanol, polyol (for example, glycerol, propylene glycol, and liquid polyethylene glycol, and the like) and suitable mixtures thereof. The proper fluidity can be maintained, for example, by the use of a coating, such as lecithin, by the maintenance of the required particle size in the case of dispersion and by the use of surfactants, stabilizing agents, cryoprotectants or antioxidants. The prevention of the action of microorganisms can be brought about by antibacterial and antifungal agents. In many cases, it will be preferable to include isotonic agents, for example, sugars or sodium chloride.

Sterile injectable solutions are prepared by incorporating the active agents in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuumdrying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Administration of Drugs and Method of Use:

As used herein, "simultaneously" is used to mean that the two agents are administered concurrently, whereas the term "in combination" is used to mean they are administered, if not simultaneously, then "sequentially" within a timeframe that they both are available to act therapeutically within the same time-frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction therebetween, and their respective half-lives.

In contrast to "in combination" or "sequentially", "separately" is used herein to mean that the gap between administering one agent and the other is significant, i.e. several hours, and this may include the case wherein the first administered agent is no longer present in the bloodstream in a therapeutically effective amount when the second agent is administered.

In an embodiment of the invention, the NTN1 neutralizing agent or the anti-netrin-1 antibody is administered sequentially or separately prior to the immune checkpoint inhibitor.

In a particularly preferred embodiment, the immune checkpoint inhibitor is administered sequentially or separately prior to the NTN1 neutralizing agent or the anti-netrin-1 antibody.

In an embodiment, both the NTN1 neutralizing agent or the anti-netrin-1 antibody as provided herein and the immune checkpoint inhibitor are within the same composition with a pharmaceutically acceptable carrier, excipient and/or diluent.

In another embodiment, they are presented under separate pharmaceutical forms or kit-of-parts. This form a composition or set or kit of parts comprising a NTN1 neutralizing agent or an anti-netrin-1 antibody and an immune checkpoint inhibitor, for a simultaneous, separate or sequential administration to a patient. Thus the invention may comprise (i) a composition comprising the two active ingredients as a mixture, or (ii) a composition comprising those active ingredients kept separate in the same conditioning or in separate conditionings, and one usually refer to the notion of a kit-of-parts in case (ii).

In an embodiment of the method of treatment, use and compositions for use, the administration is sequential or separate. The interval between both administrations may be at least 5, 10, 15, 20 or 24 hours, preferably between 24 and 96 hours, more preferably between 24 and 72 hours, or more, especially between 24 and 48 hours, for example 24 hours. In an embodiment, one agent or drug is simply administered the day after the administration of the other agent or drug.

The different pharmaceutical forms may be used in the methods of treatment of the invention, in sufficient amounts.

The invention does or may not imply a change of the dose regimen of the immune checkpoint inhibitor. However, the synergy that occurs with the NTN1 neutralizing agent or the anti-netrin-1 antibody may allow to using lower dose regimen of immune checkpoint inhibitor in a patient. The skill practitioner is able to determine the optimum dose regimen in the context of the combined treatment provided by the present invention.

The pharmaceutical compositions can be administered to a subject at a suitable dose, i.e. for the NTN1 neutralizing agent or the anti-netrin-1 antibody at least 1 mg/kg body weight, e.g. about 1 mg/kg body weight to about 100 mg/kg body weight, in particular about 10 mg/kg body weight to about 60 mg/kg body weight of the subject in which cancer, is to be treated. The immune check point inhibitor may be administered at the usual dose, or at a reduced dose with respect to the usual dose as far as the combination has a synergic efficacy. For example the dose of immune check point inhibitor is reduced by 10, 20, 30, 40, 50%, or more.

As used herein, the term "synergistic" means that the active components, e.g. antibodies, produce a greater effect when used in combination than would be expected from adding the individual effects of the two components. Advantageously, a synergistic interaction may allow for lower doses of each component to be administered to a patient, thereby decreasing the toxicity of chemotherapy, whilst producing and/or maintaining the same therapeutic effect. Thus, in a particularly preferred embodiment, each component can be administered in a sub-therapeutic amount.

TABLE 2

Description of sequences:

| SEQ ID NO: | Description | Sequence |
|---|---|---|
| 1 | NTN1 amino acid (aa) sequence (seq.) with signal peptide in bold and linear epitope mapping in bold and underlined | MMRAVWEALAALAAVACLVGAVRGGPGLSMFAGQAA QPDPCSDENGHPRRCIPDFVNAAFGKDVRVSSTCGRP PARYCVVSERGEERLRSCHLCNASDPKKAHPPAFLTDL NNPHNLTCWQSENYLQFPHNVTLTLSLGKKFEVTYVSL QFCSPRPESMAIYKSMDYGRTWVPFQFYSTQCRKMYN RPHRAPITKQNEQEAVCTDSHTDMRPLSGGLIAFSTLDG RPSAHDFDNSPVLQDWVTATDIRVAFSRLHTFGDENED |

TABLE 2-continued

Description of sequences:

| SEQ ID NO: | Description | Sequence |
|---|---|---|
| | | DSELARDSYFYAVSDLQVGGRCKCNGHAARCVRDRDD SLVCDCRHNTAGPECDRCKPFHYDRPWQRATAREANE CVACNCNLHARRCRFNMELYKLSGRKSGGVCLNCRH NTAGRHCHYCKEGYYRDMGKPITHRKACKACDCHPVG AAGKTCNQTTGQCPCKDGVTGITCNRCAKGYQQSRSPI APCIKIPVAPPTTAASSVEEPEDCDSYCKASKGKLKINMK KYCKKDYAVQIHILKADKAGDWWKFTVNIISVYKQGTSRI RRGDQSLWIRSRDIACKCPKIKPLKKYLLLGNAEDSPDQ SGIVADKSSLVIQWRDTWARRLRKFQQREKKGKCKKA |
| 2 | NTN1 nucleic acid seq. | ATGATGCGCGCAGTGTGGGAGGCGCTGGCGGCGCT GGCGGCGGTGGCGTGCCTGGTGGGCGCGGTGCGCG GCGGGCCCGGGCTCAGCATGTTCGCGGGCCAGGCG GCGCAGCCCGATCCCTGCTCGGACGAGAACGGCCAC CCGCGCCGCTGCATCCCGGACTTTGTCAATGCGGCC TTCGGCAAGGACGTGCGCGTGTCCAGCACCTGCGGC CGGCCCCCGGCGCGCTACTGCGTGGTGAGCGAGCG CGGCGAGGAGCGGCTGCGCTCGTGCCACCTCTGCAA CGCGTCCGACCCCAAGAAGGCGCACCCGCCCGCCTT CCTCACCGACCTCAACAACCCGCACAACCTGACGTG CTGGCAGTCCGAGAACTACCTGCAGTTCCCGCACAA CGTCACGCTCACACTGTCCCTCGGCAAGAAGTTCGAA GTGACCTACGTGAGCCTGCAGTTCTGCTCGCCGCGG CCCGAGTCCATGGCCATCTACAAGTCCATGGACTACG GGCGCACGTGGGTGCCCTTCCAGTTCTACTCCACGC AGTGCCGCAAGATGTACAACCGGCCGCACCGCGCGC CCATCACCAAGCAGAACGAGCAGGAGGCCGTGTGCA CCGACTCGCACACCGACATGCGCCCGCTCTCGGGCG GCCTCATCGCCTTCAGCACGCTGGACGGGCGGCCCT CGGCGCACGACTTCGACAACTCGCCCGTGCTGCAGG ACTGGGTCACGGCCACAGACATCCGCGTGGCCTTCA GCCGCCTGCACACGTTCGGCGACGAGAACGAGGAC GACTCGGAGCTGGCGCGCGACTCGTACTTCTACGCG GTGTCCGACCTGCAGGTGGGCGGCCGGTGCAAGTG CAACGGCCACGCGGCCCGCTGCGTGCGCGACCGCG ACGACAGCCTGGTGTGCGACTGCAGGCACAACACGG CCGGCCCGGAGTGCGACCGCTGCAAGCCCTTCCACT ACGACCGGCCCTGGCAGCGCGCCACAGCCCGCGAA GCCAACGAGTGCGTGGCCTGTAACTGCAACCTGCAT GCCCGGCGCTGCCGCTTCAACATGGAGCTCTACAAG CTTTCGGGGCGCAAGAGCGGAGGTGTCTGCCTCAAC TGTCGCCACAACACCGCCGGCCGCCACTGCCATTAC TGCAAGGAGGGCTACTACCGCGACATGGGCAAGCCC ATCACCCACCGGAAGGCCTGCAAAGCCTGTGATTGC CACCCTGTGGGTGCTGCTGGCAAAACCTGCAACCAA ACCACCGGCCAGTGTCCCTGCAAGGACGGCGTGACG GGTATCACCTGCAACCGCTGCGCCAAAGGCTACCAG CAGAGCCGCTCTCCCATCGCCCCCTGCATAAAGATC CCTGTAGCGCCGCCGACGACTGCAGCCAGCAGCGTG GAGGAGCCTGAAGACTGCGATTCCTACTGCAAGGCC TCCAAGGGGAAGCTGAAGATTAACATGAAAAAGTACT GCAAGAAGGACTATGCCGTCCAGATCCACATCCTGAA GGCGGACAAGGCGGGGACTGGTGGAAGTTCACGG TGAACATCATCTCCGTGTATAAGCAGGGCACGAGCC GCATCCGCCGCGGTGACCAGAGCCTGTGGATCCGCT CGCGGGACATCGCCTGCAAGTGTCCCAAAATCAAGC CCCTCAAGAAGTACCTGCTGCTGGGCAACGCGGAGG ACTCTCCGGACCAGAGCGGCATCGTGGCCGATAAAA GCAGCCTGGTGATCCAGTGGCGGGACACGTGGGCG CGGCGGCTGCGCAAGTTCCAGCAGCGTGAGAAGAAG GGCAAGTGCAAGAAGGCCTAGCG |
| 3 | NTN1 aa epitopic seq. | VACNCNLHARRCRFNMELYKLSGRKSGGVCLNCRHNT AGRHCH |
| 4 | NTN1 epitopic cDNA seq. | GTGGCCTGTAACTGCAACCTGCATGCCCGGCGCTGC CGCTTCAACATGGAGCTCTACAAGCTTTCGGGGCGC AAGAGCGGAGGTGTCTGCCTCAACTGTCGCCACAAC ACCGCCGGCCGCCACTGCCAT |
| 5 | aa seq. of CDR1-H (IMGT) | GYTFTSYN |

TABLE 2-continued

Description of sequences:

| SEQ ID NO: | Description | Sequence |
|---|---|---|
| 6 | aa seq. of CDR2-H (IMGT) | IYPGNGDT |
| 7 | aa seq. of CDR3-H (IMGT) | ARGGTGFAY |
| 8 | aa seq. of CDR1-L (IMGT) | QSVSND |
| — | aa seq. of CDR2-L (IMGT) | YAS |
| 9 | aa seq. of CDR3-L (IMGT et Kabat) | QQDYSSPWT |
| 10 | aa sequence of mouse 4C11 VH | QAYLQQSGAELVRPGASVKMSCKASGYTFTSYNMHWV KQTPRQGLEWIGAIYPGNGDTSYNQKFKGKATLTVDKS SSTAYMQLSSLTSEDSAVYFCARGGTGFAYWGQGTLV TVSA |
| 11 | aa sequence of mouse 4C11 VL | SIVMTQTPKFLLVSAGDRVTITCKASQSVSNDVAWYQQ KPGQSPKLLIYYASNRYTGVPDRFTGSGYGTDFTFTIST VQAEDLAVYFCQQDYSSPWTFGGGTKLEIK |
| 12 | Full aa sequence of 4C11 (VH + mouse IgG1 CH) | QAYLQQSGAELVRPGASVKMSCKASGYTFTSYNMHWV KQTPRQGLEWIGAIYPGNGDTSYNQKFKGKATLTVDKS SSTAYMQLSSLTSEDSAVYFCARGGTGFAYWGQGTLV TVSAAKTTPPSVYPLAPGSAAQTNSMVTLGCLVKGYFP EPVTVTWNSGSLSSGVHTFPAVLESDLYTLSSSVTVPSS PRPSETVTCNVAHPASSTKVDKKIVPRDCGCKPCICTVP EVSSVFIFPPKPKDVLTITLTPKVTCVVVDISKDDPEVQF SWFVDDVEVHTAQTQPREEQFNSTFRSVSELPIMHQD WLNGKEFKCRVNSAAFPAPIEKTISKTKGRPKAPQVYTI PPPKEQMAKDKVSLTCMITDFFPEDITVEWQWNGQPAE NYKNTQPIMNTNGSYFVYSKLNVQKSNWEAGNTFTCSV LHEGLHNHHTEKSLSHSPGK |
| 13 | Full aa sequence of 4C11 (VL + mouse Kappa CL) | SIVMTQTPKFLLVSAGDRVTITCKASQSVSNDVAWYQQ KPGQSPKLLIYYASNRYTGVPDRFTGSGYGTDFTFTIST VQAEDLAVYFCQQDYSSPWTFGGGTKLEIKRADAAPTV SIFPPSSEQLTSGGASVVCFLNNFYPKDINVKWKIDGSE RQNGVLNSWTDQDSKDSTYSMSSTLTLTKDEYERHNS YTCEATHKTSTSPIVKSFNRNEC |
| 14 | VL aa sequence of humanized variant of 4C11 | EIVMTQSPATLSVSPGERATLSCKASQSVSNDVAWYQQ KPGKAPKLLIYYASNRYTGIPPRFSGSGYGTDFTLTINNI ESEDAAYYFCQQDYSSPWTFGQG |
| 15 | VL aa sequence of humanized variant of 4C11 | DIQMTQSPSSLSASVGDRVTITCKASQSVSNDVAWFQQ RPGQSPRRLIYYASNRYTGVPSRFSGSGSGTDFTFTISS LEAEDAATYYCQQDYSSPWTFGQG |
| 16 | VL aa sequence of humanized variant of 4C11 | DIQMTQSPSSLSASVGDRVTITCKASQSVSNDVAWYQQ KPGQAPRLLIYYASNRYTGIPPRFSGSGYGTDFTLTINNI ESEDAAYYFCQQDYSSPWTFGQG |
| 17 | VL aa sequence of humanized variant of 4C11 | DIQMTQSPSSLSASVGDRVTITCKASQSVSNDVAWYLQ KPGQSPQLLIYYASNRYTGVPSRFSGSGSGTDFTFTISS LEAEDAATYYCQQDYSSPWTFGQG |
| 18 | VL aa sequence of humanized variant of 4C11 | DIVMTQTPLSLPVTPGEPASISCKASQSVSNDVAWYQQ KPGQAPRLLIYYASNRYTGIPPRFSGSGYGTDFTLTINNI ESEDAAYYFCQQDYSSPWTFGQG |
| 19 | VL aa sequence of humanized variant of 4C11 | EIVMTQSPATLSVSPGERATLSCRASQSVSNDVAWYQQ KPGQAPRLLIYYASNRYTGIPARFSGSGSGTEFTLTISSL QSEDFAVYYCQQDYSSPWTFGQG |
| 20 | VH aa sequence of humanized variant of 4C11 | QVQLVQSGAEVKKPGASVKVSCKASGYTFTSYNMHWV RQATGQGLEWMGAIYPGNGDTSYNQKFKGRVTITADK STSTAYMELSSLRSEDTAVYYCARGGTGFAYWGQG |

TABLE 2-continued

Description of sequences:

| SEQ ID NO: | Description | Sequence |
|---|---|---|
| 21 | VH aa sequence of humanized variant of 4C11 | QVQLQQSGPGLVKPSQTLSLTCAISGYTFTSYNMHWIRQPPGKGLEWIGAIYPGNGDTSYNQKFKGRVTITADKSTSTAYMELSSLRSEDTAVYYCARGGTGFAYWGQG |
| 22 | VH aa sequence of humanized variant of 4C11 | QVQLQQSGPGLVKPSQTLSLTCAISGYTFTSYNMHWVRQATGQGLEWMGAIYPGNGDTSYNQKFKGRLTISKDTSKNQVVLTMTNMDPVDTATYYCARGGTGFAYWGQG |
| 23 | VH aa sequence of humanized variant of 4C11 | EVQLVQSGAEVKKPGESLRISCKGSGYTFTSYNMHWVRQATGQGLEWMGAIYPGNGDTSYNQKFKGRFTISRDDSKNTAYLQMNSLKTEDTAVYYCARGGTGFAYWGQG |
| 24 | VH aa sequence of humanized variant of 4C11 | QVQLQESGPGLVKPSQTLSLTCTVSGYTFTSYNMHWVRQAPGQGLEWMGAIYPGNGDTSYNQKFKGRVTISVDTSKNQFSLKLSSVTAADTAVYYCARGGTGFAYWGQG |
| 25 | VH aa sequence of humanized variant of 4C11 | QVQLVQSGAEVKKPGASVKVSCKASGYTFTSYNMHWVRQATGQGLEWMGAIYPGNGDTSYNQKFKGRVTITADKSTSTAYMELSSLRSEDTAVYYCARGGTGFAYWGQG |
| 26 | VH aa sequence of humanized variant of 4C11 | QVQLQQSGPGLVKPSQTLSLTCAISGYTFTSYNMHWVRQATGQGLEWMGAIYPGNGDTSYNQKFKGRVTITADKSTSTAYMELSSLRSEDTAVYYCARGGTGFAYWGQG |
| 27 | VH aa sequence of humanized variant of 4C11 | QVQLVQSGAEVKKPGASVKVSCKASGYTFTSYNMHWVRQAPGQGLEWMGAIYPGNGDTSYAQKFKGRVTMTRDTSTSTVYMELSSLRSEDTAVYYCARGGTGFAYWGQ |
| 28 | aa seq. of CDR1-H (Kabat) | SYNMH |
| 29 | aa seq. of CDR2-H (Kabat) | AIYPGNGDTSYNQKFKG |
| 30 | aa seq. of CDR3-H (Kabat) | GGTGFAY |
| 31 | aa seq. of CDR1-L (Kabat) | KASQSVSNDVA |
| 32 | aa seq. of CDR2-L (Kabat) | YASNRYT |
| 33 | Forward primer | aaaagtactgcaagaaggactatgc |
| 34 | Reverse primer | ccctgcttatacacggagatg |
| 35 | NTN1 aa epitopic seq. | ARRCRFNMELYKLSGRKSGGVC |
| 36 | NTN1 epitopic cDNA seq. | GCCCGGCGCTGCCGCTTCAACATGGAGCTCTACAAGCTTTCGGGGCGCAAGAGCGGAGGTGTCTGC |

CDRs under IMGT are highlighted in bold in Table 1 where appropriate.

The invention will now be described using non-limiting examples referring to the figures.

FIG. 1: Mice were grafted with EMT-6 mammary cell line and treated with anti-netrine-1 interfering drug (HUM03); with control antibody (NP006); with HUM03+anti-CTLA-4 or NP006+ anti-CTLA-4 (n=12 animals/group). Tumor volume was externally measured and total regression of tumor volume was quantified 28 days after implantation. The table is showing the number of mice without tumor after 28 days.

FIG. 2: Same as FIG. 1 but the figure is showing the percentage of mice survival quantified after Kaplan-Mayer analysis up to 80 days post implantation of EMT-6 mammary tumor (P=0.046).

Figure 3:
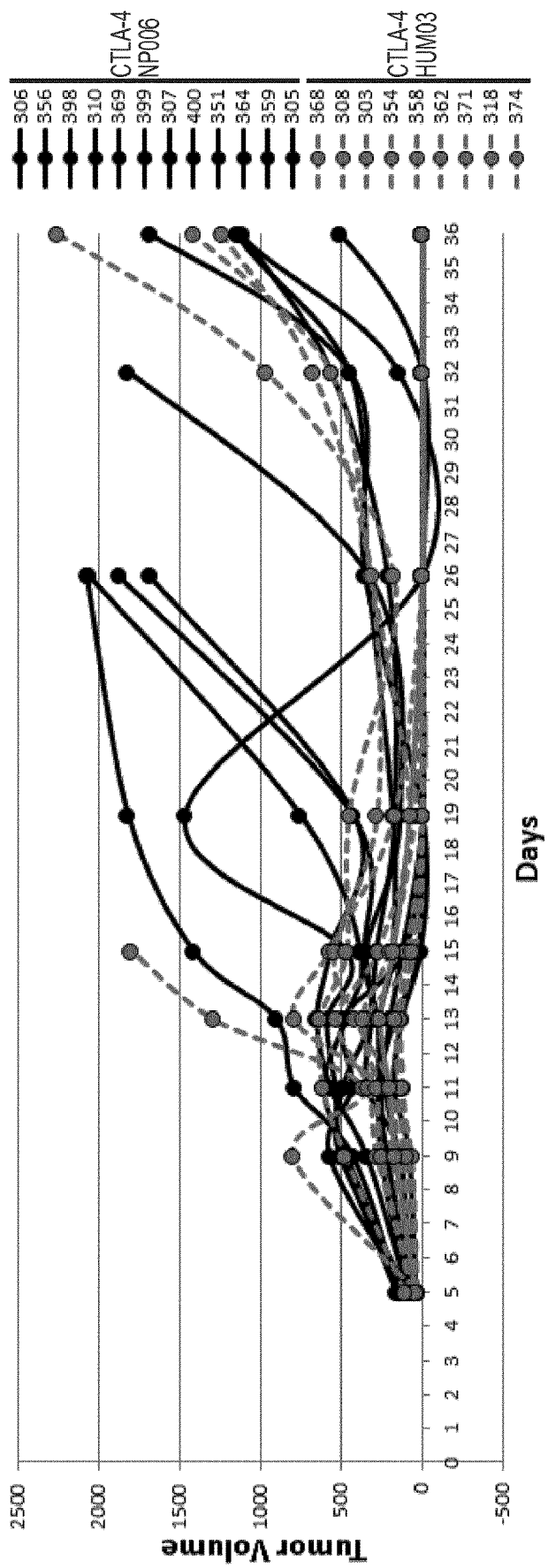

FIG. 3: Same experiment as in FIGS. 1 and 2 but tumor growth of each animal is shown. Sacrifice of animal is indicated by †.

FIG. 4: Same type of experiment as in FIG. 1-2-3 but mice were grafted with 4T1 mammary cancer cell line and treated with HUM03+anti-PD-1 or NP001+ anti-PD-1 (n=7 animals/group). Mice survival was quantified by Kaplan-Mayer analysis at day 25 (P=0.0411).

Figure 5:
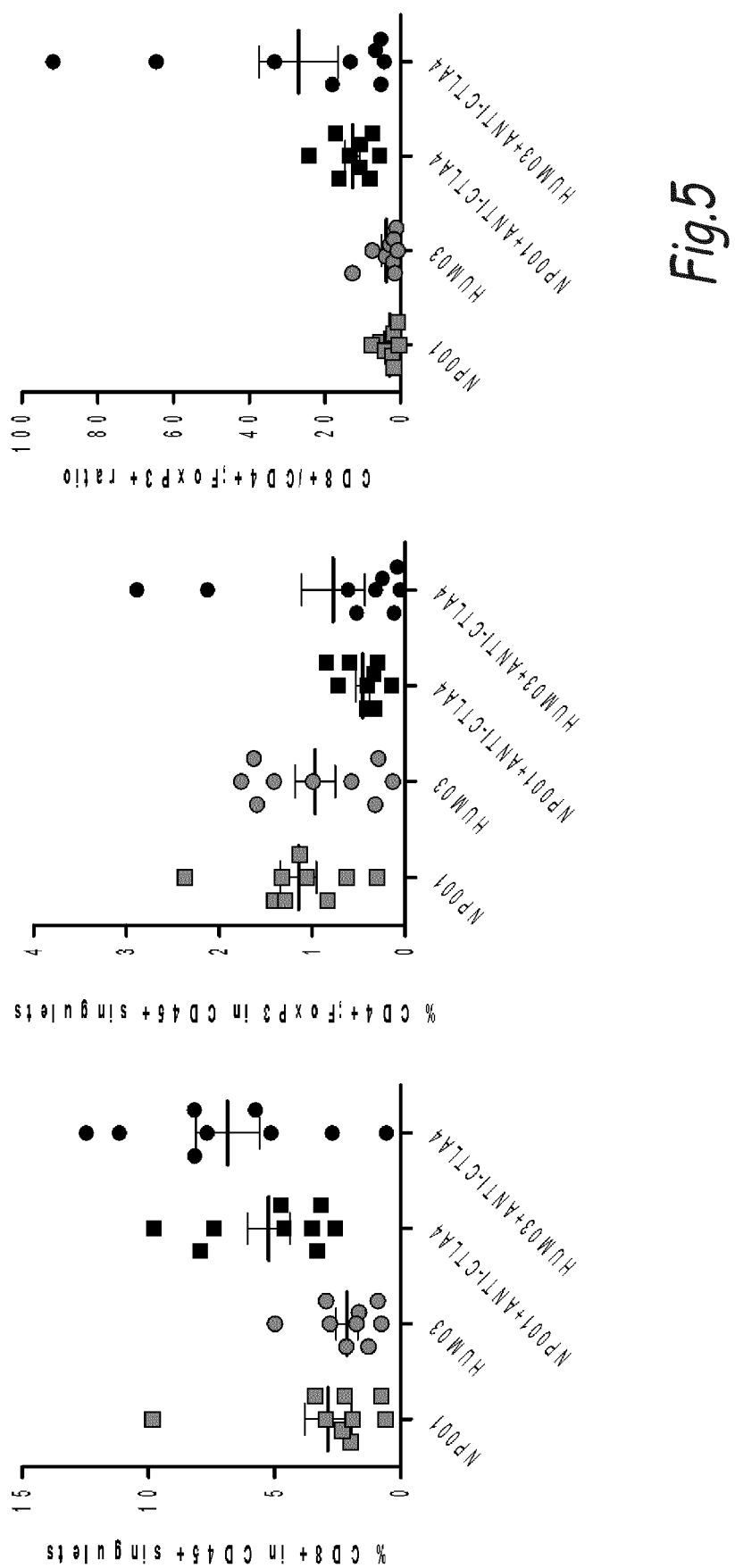

FIG. 5: Combination of HUM03 with anti-CTLA4 modulates tumoral T cell effector/Treg balance in the syngeneic EMT6 xenograft mice model. $10^6$ EMT6 cells were subcutaneously grafted in the flank of BalbCJ 8 weeks female mice. Animals were randomly separated in 4 groups treated 3 times (e.g. at day 10, 14, 18) by HUM03 (10 mg/Kg I.P.) or NP001 IgG1 control isotype, alone or in association with anti-CTLA4 (BioX cell-clone 9H10-20 mg/Kg I.P.). EMT6 tumors were dissociated individually and analyzed by flow cytometry with exhaustive lymphoid and myeloid staining panels. Here we focus on the CD8 T cell effector (left), the CD4; FoxP3 TReg (middle) and the balance between them (right). As seen in the right panel, in the combination HUM03/CTLA4 mAb the balance T Cell effector/T regulator is move toward T Cell effector.

EXAMPLE 1

Materials and Methods

Cell Lines:

Murine mammary carcinoma EMT6 (ATCC® CRL2755™-LGC standards-France) cells were cultured in Eagle's Minimum Essential Medium complemented with 10% of Fetal Bovine Serum and antibiotics (Streptomycin and Penicillin).

*Mus Musculus* mammary gland 4T1 (ATCC® CRL-2539™ LGC standards-France) cells were cultured in Dulbecco's Modified Eagle Medium (DMEM), 10% FBS.

Mice Experiments:

Mice were maintained in a specific pathogen-free animal facility and handled in accordance with the institutional guidelines and protocols approved by the animal care and use committee (Comité d'Evaluation Commun au Centre Léon Bérard, à l'Animalerie de transit de l'ENS, au PBES et au laboratoire P4; CECCAP).

$5.10^5$ or $10.10^5$ EMT6 cells were subcutaneously grafted in the flank of BalbC/J 8 weeks female mice. All animals were treated 3 times by 400 µg/injection of anti-CTLA4 (BioX cell USA-clone 9H10-) at day 7, 11 and 14. Animals were randomly separated in 4 groups treated with HUM03; NP006 IgG1 control isotype (Netris Pharma, France); HUM03+anti-CTLA4 and NP001+anti-CTLA-4 respectively. NP006 and HUM03 antibodies were intraperitoneally administrated trice's a week at 10 mg/Kg. Tumor were measured two times weekly by external calipers. Tumor progression was determined after 29 days post-graft. When tumors reached a volume of 2000 mm³, mice were sacrificed and survival determine.

$5.10^5$ 4 T1 cells were subcutaneously grafted in the flank of BalbC/J 7 weeks female mice. Animals were treated two weeks by 100 µg/injection of anti-PD1 antibody in the corresponding groups (BioX cell USA-clone RMP1-14). Animals were randomly separated in 3 groups treated with PBS; HUM03+anti-PD-1 and NP001 (Netris Pharma, France)+anti-PD1, respectively. Tumors were measured three times weekly by external calipers. When tumors reached a volume of 1500 mm³, mice were sacrificed and survival determined.

Statistics:

Statistics were performed using GraphPad software, student T test were two-sided and a P value of less than 0.05 was considered statistically significant Survival curves were generated by the Kaplan-Meier method on GraphPad software. Data were analysed with a Mantel-Cox test. n indicates the number of repeats. All statistical tests were two-sided and a P value of less than 0.05 was considered statistically significant.

Results/Discussion

1) Combining HUM03 and CTLA4 mAb Delays Tumor Relapse and Increase Mice Survival of EMT6 Breast Cancer Model.

To test the combination of anti-Netrin-1 mAb and anti-CTLA4, mammary EMT-6 cancer cells were grafted in BalbC/J mice.

As presented in FIGS. 1-3, combining HUM03 with the immune checkpoint inhibitor CTLA4 is massively enhancing the anti-tumor response observed with CTLA4 alone. The number of mice without tumor at day 28 of treatment is moving from respectively 0/12 in the HUM03 alone group and 2/12 in the CTLA4 alone group to 8/12 in the combo treatment (FIG. 1).

Survival of mice was also quantified after Kaplan Mayer analysis during 80 days (p=0.046) and it shows that the combination significantly increase mice survival (FIG. 2) and this appears to be associated to a longer disease control by the combination therapy (FIG. 3). To analyse whether this increased activity of the combination is restricted to CTLA4 or can be extended to other immune checkpoint inhibitor, we next analyzed the effect of the combination HUM03 with PD-1.

2) Combining HUM03 and PD-1 mAb Increase Mice Survival of 4T1 Breast Cancer Model.

To test the combination of anti-Netrin-1 mAb and anti-PD1, mammary gland 4T1 cancer cells were grafted in BalbC/J mice. As presented in FIG. 4, mice survival was quantified after Kaplan Mayer analysis 20 days after graft (p=0.0411)(FIG. 4). Similarly to what is observed with CTLA4, the combination PD-1/HUM03 is more efficient than PD-1 alone. Indeed, while the monotherapy PD1 mAb alone is associated with no increase survival (4 out of 7 mice were alive at day 20 similarly to what is observed in the control treatment group), combining HUM03 to PD1 is increasing the mice survival to 100% (7 out of 7 mice alive at day 20).

Together these data support the view that combining HUM03 to the current immunotherapeutic treatments is boosting their efficacy. In a search of the mechanism that may explain this enhanced effect of immune checkpoint inhibitors in presence of netrin-1 interference, we analyse the tumor immune infiltrate in response to monotherapy or combination treatment.

3) Combining HUM03 and CTLA4 mAb Favor Tumoral T Cell Effectors/T Regulators Ratio in the Model of EMT6 Breast Cancer.

To analyse the effect of the combination of anti-Netrin-1 mAb and anti-CTLA4 in tumor immune infiltrate, mammary EMT-6 cancer cells were grafted in BalbC/J mice as presented above and treated either with HUM03 alone (vs control isotype NP001), CTLA4 alone or the combination HUM03+CTLA4 mAb. Tumors were dissociated and lymphoid cells content was analyzed by flow cytometry. As presented in FIG. 5, while the monotherapy (either HUM03 or CTLA4) is not affecting significantly the ratio T cell effector/T cell regulator, the combination is shifting the ratio toward T cell effector. This supports the increased efficacy by suggesting that the combination is enhancing the presence of the killer lymphoid cells (T cell effector).

EXAMPLE 2

$5.10^5$ EO771 cells were subcutaneously grafted in the flank of C57b6J 8 weeks female mice. 6 days after graft, animals were randomly separated in 4 groups treated with NP137 or NP001 IgG1 control isotype alone or in combination with the anti-PD-1 antibody. All animals were treated twice a week by IP route with anti-CTLA4 (BioXcell-clone 9H10) at 20 mg/Kg and/or NP antibodies at 10 mg/Kg. Tumor volumes were measured twice a week by external calipers. When tumors reached a volume of 2000 mm$^3$, mice were sacrificed.

$5.10^5$ MC38 cells were subcutaneously grafted in the flank of C57b6J 8 weeks female mice. 6 days after graft, animals were randomly separated in 4 groups treated with NP137 or NP001 IgG1 control isotype alone or in combination with the anti-PD-1 antibody. All animals were treated twice a week by IP route with anti-PD-1 (BioXcell-clone RMP1-14) at 5 mg/Kg and/or NP antibodies at 10 mg/Kg. Tumor volumes were measured twice a week by external calipers. When tumors reached a volume of 2000 mm$^3$, mice were sacrificed.

$5.10^6$ 0016 eM3 cells were subcutaneously grafted in the flank of C57b6J 8 weeks female mice. 6 days after graft, animals were randomly separated in 4 groups treated with NP137 or NP001 IgG1 control isotype alone or in combination with the anti-PD-1 antibody. All animals were treated twice a week by IP route with anti-PD-1 (BioXcell-clone RMP1-14) at 5 mg/Kg and/or NP antibodies at 10 mg/Kg. Tumor volumes were measured twice a week by external calipers. When tumors reached a volume of 2000 mm$^3$, mice were sacrificed.

EMT-6 and 4T1 cells (see Example 1) were also used in similar conditions.

The following table demonstrates the potentiation or synergy resulting from the combination of NP137 and anti-PD1 antibodies.

| | | | Response | | |
|---|---|---|---|---|---|
| Cell line | Organ | ICI used | NP137 | ICI | ICI + NP137 |
| EMT-6 | Breast cancer | CTLA-4 | − | ++ | +++ |
| EO771 | Breast cancer | CTLA-4 | − | +++ | ++++ |
| 4T1 | Breast cancer | PD1 | − | − | + |
| 0016eM3 | Melanoma | PD1 | − | +++ | ++++ |
| MC38 | Colon cancer | PD1 | − | + | ++ |

This application includes a sequence listing:

Filename—"Seq. Listing.txt"

Date of creation—Aug. 8, 2021

Size—36,700 bytes

The invention claimed is:

1. A method of anti-cancer treatment consisting of administering to a patient in need thereof of an effective amount of an anti-netrin-1 antibody and an immunotherapeutic agent comprising an immune checkpoint inhibitor, wherein the anti-netrin-1 antibody comprises:
   (i) a variable domain VH comprising a CDR1-H of sequence SEQ ID NO: 5, a CDR2-H of sequence SEQ ID NO: 6, a CDR3-H of sequence SEQ ID NO: 7, and a variable domain VL comprising a CDR1-L of sequence SEQ ID NO: 8, a CDR2-L of sequence YAS and a CDR3-L of sequence SEQ ID NO: 9, or
   (ii) comprises a variable domain VH comprising a CDR1-H of sequence SEQ ID NO: 28, a CDR2-H of sequence SEQ ID NO: 29, a CDR3-H of sequence SEQ ID NO: 30, and a variable domain VL comprising a CDR1-L of sequence SEQ ID NO: 31, a CDR2-L of sequence SEQ ID NO: 32 and a CDR3-L of sequence SEQ ID NO: 9;
   wherein the immune checkpoint inhibitor is selected from the group consisting of anti-PD1, anti-PD-L1, anti-PD-L2 and anti-CTLA-4 antibodies.

2. The method of claim 1, wherein the anti-netrin-1 antibody comprises the amino acid sequence SEQ ID NO: 10, 11, 12 or 13.

3. The method of claim 1, wherein the anti-netrin-1 antibody comprises both sequences SEQ ID NO: 10 and 11, or both sequences SEQ ID NO: 12 and 13.

4. The method of claim 1, wherein the anti-netrin-1 antibody comprises an amino acid sequence selected from the group consisting of SEQ ID NO: 14, SEQ ID NO: 15, SEQ ID NO: 16, SEQ ID NO: 17, SEQ ID NO: 18 and SEQ ID NO: 19.

5. The method of claim 1, wherein the anti-netrin-1 antibody comprises an amino acid sequence selected from the group consisting of SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27.

6. The method of claim 1, wherein the anti-netrin-1 antibody comprises an amino acid sequence selected from the group consisting of SEQ ID NO: 14, SEQ ID NO: 15, SEQ ID NO: 16, SEQ ID NO: 17, SEQ ID NO: 18 and SEQ ID NO: 19 and an amino acid sequence selected from the group consisting of SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27.

7. The method of claim 1, wherein the anti-netrin-1 antibody comprises pairs of VH and VL amino acid sequences selected from the group consisting of SEQ ID NO: 20 and 14, SEQ ID NO: 21 and 15, SEQ ID NO: 22 and 16, SEQ ID NO: 23 and 17, SEQ ID NO: 24 and 17, SEQ ID NO: 25 and 16, SEQ ID NO: 26 and 17, SEQ ID NO: 22 and 17, SEQ ID NO: 25 and 18, SEQ ID NO: 21 and 16, the SEQ ID NO: 27 and 19.

8. The method of claim 1, wherein the anti-netrin-1 antibody comprises a heavy chain comprising a VH having the sequence as set forth in SEQ ID NO: 22 and a Human IgG1 heavy chain constant domain, and a VL having the sequence as set forth in SEQ ID NO: 16 and a Human light chain constant domain.

9. A method of anti-cancer treatment consisting of administering to a patient in need thereof an effective amount of an anti-netrin-1 antibody and of an immune checkpoint inhibitor, wherein the immune checkpoint inhibitor is selected from the group consisting of anti-PD1, anti-PD-L1, anti-PD-L2 and anti-CTLA-4 antibodies, and wherein the anti-netrin-1 antibody comprises:
   (i) a variable domain VH comprising a CDR1-H of sequence SEQ ID NO: 5, a CDR2-H of sequence SEQ ID NO: 6, a CDR3-H of sequence SEQ ID NO: 7, and a variable domain VL comprising a CDR1-L of sequence SEQ ID NO: 8, a CDR2-L of sequence YAS and a CDR3-L of sequence SEQ ID NO: 9, or (ii) a variable domain VH comprising a CDR1-H of sequence SEQ ID NO: 28, a CDR2-H of sequence SEQ ID NO: 29, a CDR3-H of sequence SEQ ID NO: 30, and a variable domain VL comprising a CDR1-L of sequence SEQ ID NO: 31, a CDR2-L of sequence SEQ ID NO: 32 and a CDR3-L of sequence SEQ ID NO: 9.

10. The method of claim 9, wherein the anti-netrin-1 antibody comprises a heavy chain comprising a VH having the sequence as set forth in SEQ ID NO: 22 and a Human IgG1 heavy chain constant domain, and a VL having the sequence as set forth in SEQ ID NO: 16 and a Human light chain constant domain.

* * * * *